US008708998B2

(12) United States Patent
Weston et al.

(10) Patent No.: US 8,708,998 B2
(45) Date of Patent: Apr. 29, 2014

(54) ENCLOSURE-BASED REDUCED PRESSURE TREATMENT SYSTEM

(75) Inventors: Richard Scott Weston, Carlsbad, CA (US); Timothy Robert Johnson, Ocean Beach, CA (US); Michael Seth Miller, Linton, IN (US)

(73) Assignee: BlueSky Medical Group, Inc., Memphis, TN (US)

( * ) Notice: Subject to any disclaimer, the term of this patent is extended or adjusted under 35 U.S.C. 154(b) by 832 days.

(21) Appl. No.: 12/419,542

(22) Filed: Apr. 7, 2009

(65) Prior Publication Data

US 2009/0192499 A1 Jul. 30, 2009

Related U.S. Application Data

(62) Division of application No. 11/075,020, filed on Mar. 8, 2005, now Pat. No. 8,100,887.

(60) Provisional application No. 60/551,951, filed on Mar. 9, 2004.

(51) Int. Cl.
*A61M 27/00* (2006.01)
*A61M 1/00* (2006.01)

(52) U.S. Cl.
USPC .......................................... 604/543; 604/313

(58) Field of Classification Search
USPC ......... 604/292–293, 313, 315–316, 319, 541, 604/543, 317, 320
See application file for complete search history.

(56) References Cited

U.S. PATENT DOCUMENTS

| 59,388 | A | 11/1866 | Hadfield |
| 765,746 | A | 7/1904 | Miner |

(Continued)

FOREIGN PATENT DOCUMENTS

| CA | 2103033 C | 11/1992 |
| CA | 2414393 A1 | 11/1992 |

(Continued)

OTHER PUBLICATIONS

U.S. Appl. No. 12/186,424, filed Aug. 5, 2008, Krohn.

(Continued)

*Primary Examiner* — Melanie Hand
*Assistant Examiner* — Paula Craig
(74) *Attorney, Agent, or Firm* — Knobbe, Martens, Olson & Bear LLP

(57) ABSTRACT

A reduced pressure treatment appliance is provided for enclosing and providing reduced pressure treatment to a portion of a body of a patient. The reduced pressure treatment appliance may be used to treat wounds and other conditions, such as lymphedema, varicose veins, venous insufficiency and stasis, and other infirmities. In some embodiments, the appliance comprises an enclosure that encloses the portion of the body to be treated for purposes of applying a reduced pressure to the enclosed portion of the body. In other embodiments, the wound treatment appliance also includes a vacuum system to supply reduced pressure to the portion of the body to be treated in the volume under the enclosure. In yet other embodiments, the treatment appliance also includes wound packing means to prevent overgrowth of the wound or to encourage growth of wound tissue into an absorbable matrix comprising the wound packing means. In still other embodiments, a suction bulb may be used to provide a source of reduced pressure to an enclosure that encloses the portion of the body to be treated. Finally, methods are provided for using various embodiments of the treatment appliance.

23 Claims, 5 Drawing Sheets

(56) References Cited

U.S. PATENT DOCUMENTS

| | | | |
|---|---|---|---|
| 846,674 A | 7/1907 | Funk | |
| 1,355,679 A | 10/1920 | McConnell | |
| 1,355,846 A | 10/1920 | Rannells | |
| 1,385,346 A | 7/1921 | Taylor | |
| 1,480,562 A | 1/1924 | Mock | |
| 1,585,104 A | 5/1926 | Montgomery | |
| 1,629,108 A | 5/1927 | Lake | |
| 1,732,310 A | 10/1929 | Naibert | |
| 1,936,129 A | 12/1931 | Fisk | |
| 1,863,534 A | 6/1932 | Odell | |
| 2,232,254 A | 2/1941 | Morgan | |
| 2,280,915 A | 4/1942 | Johnson | |
| 2,338,339 A | 1/1944 | La Mere et al. | |
| 2,366,799 A | 1/1945 | Luisada | |
| 2,385,683 A | 9/1945 | Burton | |
| 2,547,758 A | 4/1951 | Keeling | |
| 2,969,057 A | 1/1961 | Simmons | |
| 3,026,526 A | 3/1962 | Montrose | |
| 3,315,665 A | 10/1963 | MacLeod | |
| 3,217,707 A | 11/1965 | Werding | |
| 3,238,937 A | 3/1966 | Stein | |
| 3,286,711 A | 11/1966 | MacLeod | |
| 3,367,332 A | 2/1968 | Groves | |
| 3,465,748 A | 9/1969 | Kravchenko | |
| 3,478,736 A | 11/1969 | Roberts et al. | |
| 3,486,504 A | 12/1969 | Austin, Jr. | |
| 3,572,340 A | 3/1971 | Lloyd et al. | |
| 3,610,238 A | 10/1971 | Rich, Jr. | |
| 3,682,180 A | 8/1972 | McFarlane | |
| 3,712,298 A | 1/1973 | Snowdon et al. | |
| 3,727,629 A | 4/1973 | Gifford | |
| 3,794,035 A | 2/1974 | Brenner | |
| 3,826,254 A | 7/1974 | Mellor | |
| 3,859,989 A | 1/1975 | Spielberg | |
| 3,874,387 A | 4/1975 | Barbieri | |
| 3,896,810 A | 7/1975 | Akiyama | |
| 3,908,664 A | 9/1975 | Loseff | |
| 3,954,105 A | 5/1976 | Nordby et al. | |
| 3,961,625 A | 6/1976 | Dillon | |
| 3,988,793 A | 11/1976 | Abitbol | |
| 3,993,080 A | 11/1976 | Loseff | |
| RE29,319 E | 7/1977 | Nordby et al. | |
| 4,080,970 A | 3/1978 | Miller | |
| 4,102,342 A | 7/1978 | Akiyama et al. | |
| 4,112,947 A | 9/1978 | Nehring | |
| 4,139,004 A * | 2/1979 | Gonzalez, Jr. | 602/14 |
| 4,149,541 A | 4/1979 | Gammons et al. | |
| 4,169,563 A | 10/1979 | Leu | |
| 4,172,455 A | 10/1979 | Beaussant | |
| 4,224,945 A | 9/1980 | Cohen | |
| 4,250,882 A | 2/1981 | Adair | |
| 4,256,109 A | 3/1981 | Nichols | |
| 4,261,363 A | 4/1981 | Russo | |
| 4,275,721 A | 6/1981 | Olson | |
| 4,297,995 A | 11/1981 | Golub | |
| 4,353,359 A * | 10/1982 | Milbauer | 601/166 |
| 4,373,519 A | 2/1983 | Errede et al. | |
| 4,382,441 A | 5/1983 | Svedman | |
| 4,392,853 A | 7/1983 | Muto | |
| 4,396,023 A | 8/1983 | Anderson | |
| 4,419,097 A | 12/1983 | Rowland | |
| 4,421,109 A | 12/1983 | Thornton | |
| 4,432,354 A | 2/1984 | Lasley | |
| 4,465,485 A | 8/1984 | Kashmer et al. | |
| 4,469,092 A | 9/1984 | Marshall et al. | |
| 4,475,909 A | 10/1984 | Eisenberg | |
| 4,480,638 A | 11/1984 | Schmid | |
| 4,523,920 A | 6/1985 | Russo | |
| 4,525,166 A | 6/1985 | Leclerc | |
| 4,527,064 A | 7/1985 | Anderson | |
| 4,533,352 A | 8/1985 | Van Beek et al. | |
| 4,540,412 A | 9/1985 | Van Overloop | |
| 4,543,100 A | 9/1985 | Brodsky | |
| 4,573,965 A | 3/1986 | Russo | |
| 4,605,399 A | 8/1986 | Weston et al. | |
| 4,608,041 A | 8/1986 | Nielsen | |
| 4,624,656 A | 11/1986 | Clark et al. | |
| 4,640,688 A | 2/1987 | Hauser | |
| 4,691,695 A | 9/1987 | Birk et al. | |
| 4,738,249 A | 4/1988 | Linman | |
| 4,743,232 A | 5/1988 | Kruger | |
| 4,759,354 A | 7/1988 | Quarfoot | |
| 4,764,167 A | 8/1988 | Tu | |
| 4,765,316 A | 8/1988 | Marshall | |
| 4,768,501 A * | 9/1988 | George | 602/6 |
| 4,778,456 A | 10/1988 | Lokken | |
| 4,790,833 A | 12/1988 | Schmidt | |
| 4,820,265 A | 4/1989 | DeSatnick et al. | |
| 4,820,284 A | 4/1989 | Hauri | |
| 4,828,546 A | 5/1989 | McNeil et al. | |
| 4,834,110 A | 5/1989 | Richard | |
| 4,836,192 A | 6/1989 | Abbate | |
| 4,838,883 A | 6/1989 | Matsuura | |
| 4,840,187 A | 6/1989 | Brazier | |
| 4,851,545 A | 7/1989 | Song et al. | |
| 4,863,449 A | 9/1989 | Therriault et al. | |
| 4,878,901 A | 11/1989 | Sachse | |
| 4,906,233 A | 3/1990 | Moriuchi et al. | |
| 4,917,112 A | 4/1990 | Kalt | |
| 4,921,488 A | 5/1990 | Maitz et al. | |
| 4,921,492 A | 5/1990 | Schultz | |
| 4,925,447 A | 5/1990 | Rosenblatt | |
| 4,931,519 A | 6/1990 | Song et al. | |
| 4,941,882 A | 7/1990 | Ward et al. | |
| 4,950,483 A | 8/1990 | Ksander | |
| 4,953,565 A | 9/1990 | Tachibana et al. | |
| 4,969,880 A | 11/1990 | Zamierowski | |
| 4,969,881 A | 11/1990 | Viesturs | |
| 5,000,164 A | 3/1991 | Cooper | |
| 5,035,884 A | 7/1991 | Song et al. | |
| 5,086,764 A | 2/1992 | Gilman | |
| 5,100,396 A | 3/1992 | Zamierowski | |
| 5,106,362 A | 4/1992 | Gilman | |
| 5,113,871 A | 5/1992 | Viljanto et al. | |
| 5,149,331 A | 9/1992 | Ferdman et al. | |
| 5,228,431 A | 7/1993 | Giarretto | |
| 5,243,968 A | 9/1993 | Byun | |
| 5,261,893 A | 11/1993 | Zamierowski | |
| 5,362,543 A | 11/1994 | Nickerson | |
| 5,425,742 A | 6/1995 | Joy | |
| 5,437,651 A | 8/1995 | Todd et al. | |
| 5,462,514 A | 10/1995 | Harris | |
| 5,489,280 A | 2/1996 | Russell | |
| 5,514,166 A | 5/1996 | Silver et al. | |
| 5,527,293 A | 6/1996 | Zamierowski | |
| 5,549,584 A | 8/1996 | Gross | |
| 5,636,643 A | 6/1997 | Argenta | |
| 5,645,081 A | 7/1997 | Argenta | |
| 5,688,225 A | 11/1997 | Walker | |
| 5,701,917 A | 12/1997 | Khouri | |
| 5,716,411 A | 2/1998 | Orgill et al. | |
| 5,827,246 A | 10/1998 | Bowen | |
| 5,830,496 A | 11/1998 | Freeman | |
| 5,848,998 A * | 12/1998 | Marasco, Jr. | 604/290 |
| 5,865,772 A * | 2/1999 | George | 602/3 |
| 5,893,368 A | 4/1999 | Sugerman | |
| 5,938,626 A | 8/1999 | Sugerman | |
| 5,970,266 A | 10/1999 | Takato | |
| 6,045,541 A | 4/2000 | Matsumoto | |
| 6,135,116 A | 10/2000 | Vogel et al. | |
| D434,150 S | 11/2000 | Tumey et al. | |
| 6,142,982 A | 11/2000 | Hunt | |
| 6,176,307 B1 | 1/2001 | Danos et al. | |
| 6,287,521 B1 | 9/2001 | Quay et al. | |
| 6,332,631 B1 | 12/2001 | Kirk | |
| 6,371,976 B1 | 4/2002 | Vrzalik | |
| 6,458,109 B1 | 10/2002 | Henley et al. | |
| 6,471,685 B1 | 10/2002 | Johnson | |
| 6,536,056 B1 | 3/2003 | Vrzalik et al. | |
| 6,547,756 B1 | 4/2003 | Greter et al. | |
| 6,595,949 B1 | 7/2003 | Shapiro | |
| 6,673,028 B1 | 1/2004 | Argenta et al. | |
| 6,685,681 B2 | 2/2004 | Lockwood et al. | |
| 6,936,037 B2 | 8/2005 | Bubb et al. | |

(56) References Cited

U.S. PATENT DOCUMENTS

| | | | |
|---|---|---|---|
| 6,951,553 | B2 | 10/2005 | Bubb et al. |
| 6,979,324 | B2 | 12/2005 | Bybordi et al. |
| 6,988,423 | B2 | 1/2006 | Bolam et al. |
| 6,994,702 | B1 | 2/2006 | Johnson |
| 7,004,915 | B2 | 2/2006 | Boynton et al. |
| 7,070,584 | B2 | 7/2006 | Johnson et al. |
| 7,077,832 | B2 | 7/2006 | Fleischmann |
| 7,108,683 | B2 | 9/2006 | Zamierowski |
| 7,117,869 | B2 | 10/2006 | Heaton et al. |
| 7,128,735 | B2 | 10/2006 | Weston |
| 7,144,390 | B1 | 12/2006 | Hannigan et al. |
| 7,214,202 | B1 | 5/2007 | Vogel et al. |
| 7,216,651 | B2 | 5/2007 | Argenta et al. |
| 7,235,066 | B1 | 6/2007 | Narini et al. |
| 7,279,612 | B1 | 10/2007 | Heaton et al. |
| 8,100,887 | B2 * | 1/2012 | Weston et al. ............. 604/543 |
| 2002/0068913 | A1 | 6/2002 | Fleischmann |
| 2002/0115952 | A1 | 8/2002 | Tumey et al. |
| 2002/0143286 | A1 | 10/2002 | Tumey |
| 2002/0161346 | A1 | 10/2002 | Lockwood et al. |
| 2002/0183702 | A1 | 12/2002 | Henley et al. |
| 2002/0198503 | A1 | 12/2002 | Risk |
| 2002/0198504 | A1 | 12/2002 | Risk |
| 2003/0014025 | A1 | 1/2003 | Allen et al. |
| 2003/0040687 | A1 | 2/2003 | Boynton et al. |
| 2003/0050594 | A1 | 3/2003 | Zamierowski |
| 2003/0108587 | A1 | 6/2003 | Orgill et al. |
| 2003/0125646 | A1 | 7/2003 | Whitlock |
| 2003/0225347 | A1 | 12/2003 | Argenta et al. |
| 2004/0073151 | A1 | 4/2004 | Weston |
| 2004/0163278 | A1 * | 8/2004 | Caspers et al. ............. 36/3 R |
| 2005/0020955 | A1 | 1/2005 | Wilkes et al. |
| 2005/0148913 | A1 | 7/2005 | Weston |
| 2005/0203452 | A1 | 9/2005 | Weston |
| 2005/0222527 | A1 | 10/2005 | Miller et al. |
| 2005/0222528 | A1 | 10/2005 | Weston |
| 2005/0222544 | A1 | 10/2005 | Weston |
| 2005/0261615 | A1 | 11/2005 | Weston |
| 2005/0261642 | A1 | 11/2005 | Weston |
| 2005/0261643 | A1 | 11/2005 | Bybordi et al. |
| 2007/0014837 | A1 | 1/2007 | Johnson et al. |
| 2007/0021697 | A1 | 1/2007 | Ginther et al. |
| 2007/0239139 | A1 | 10/2007 | Weston et al. |

FOREIGN PATENT DOCUMENTS

| | | |
|---|---|---|
| CA | 2157772 C | 9/1995 |
| CA | 2198243 A1 | 2/1996 |
| CA | 2237606 A1 | 5/1997 |
| CA | 2238413 A1 | 5/1997 |
| CA | 2551340 A1 | 5/1997 |
| CA | 2280817 A1 | 2/1998 |
| CA | 2303085 A1 | 3/1999 |
| CA | 2471780 A1 | 3/1999 |
| CA | 2347115 A1 | 4/2000 |
| CA | 2367460 A1 | 10/2000 |
| CA | 2390513 A1 | 5/2001 |
| CA | 2408305 A1 | 11/2001 |
| CA | 2351342 A1 | 6/2002 |
| CA | 2442724 A1 | 10/2002 |
| CA | 2432293 A1 | 2/2003 |
| CA | 2368085 C | 5/2006 |
| DE | 561757 | 10/1932 |
| DE | 2809828 | 9/1978 |
| DE | 3935818 | 10/1990 |
| DE | 4111122 | 4/1993 |
| EP | 1 897 569 B1 | 8/2002 |
| GB | 114754 | 4/1918 |
| GB | 641061 | 8/1950 |
| GB | 1273342 | 5/1972 |
| GB | 2195255 A | 4/1988 |
| GB | 2342584 A | 4/2000 |
| RU | 240188 | 3/1969 |
| WO | WO 90/11795 | 10/1990 |
| WO | WO 91/00718 | 1/1991 |
| WO | WO 91/16030 | 10/1991 |
| WO | WO 92/19313 | 11/1992 |
| WO | WO 92/20299 | 11/1992 |
| WO | WO 96/05873 | 2/1996 |
| WO | WO 2005/115497 | 12/2005 |

OTHER PUBLICATIONS

"General Characteristics of Wound Healing and Russian Classification of Wound Healing Process."

"Pleur-evac. Adult-Pediatric, Non-Metered." Code Number: A-4000. Control No. F7961J, 1 page.

3M Health Care, Controlling the Risk of Surgical Site Infections after Cardiovascular Procedures: The Importance of Providing a Sterile Surface, *Brochure*, St. Paul, MN and London, Ontario, Canada, 1997, 8 pages.

A Sensational Medical discovery, *Brit. Journ. Nurs.*, Jul. 15, 1911, 42.

Aeros, "Moblvac II," 1 page.

Aeros, Aeros Instruments, Inc. 1111 Lakeside Dr., Gurnee, IL 60031. Aug. 1993. "Care-E-Vac," 2 pages.

Aeros, Aeros Insturments, Inc. 3411 Commercial Ave., Northbrook, IL 60062. Oct. 1988. Part No. 1504-02 7M. "Instavac Aspirator," 1 page.

Agarwala, S., et al., Use of Mini-Vacuum Drains in Small Surgical Wounds, *Plastic and Reconstructive Surgery*, Apr. 1998, 101(5), 1421-1422 (Correspondence).

Agrama, H.M., Functional Longevity of Intraperitoneal Drains, *Amer. Journ. of Surg.*, Sep. 1976, 132, 418-421.

Alexander, J. Wesley, "Prevention of Wound Infections," The American Journal of Surgery, Jul. 1976, pp. 59-63, vol. 132, USA.

Alper, J.C., et al., An Effective Dressing for a Large, Draining Abdominal wound, *RN*, Dec. 1988, 24-25.

Alper, J.C., et al., Moist Wound Healing under a Vapor Permeable Membrane, *Journ. of Amer. Acad. of Derm.*, Mar. 1983, 8(3), 347-353.

Alper, Joseph, C., "Recent Advances in Moist Wound Healing," Southern Medical Journal, Nov. 1986, pp. 1398-1404, vol. 79, No. 11 USA.

Antonic, M., LJ. Spasenovic, S. Ilic, Experience with the Use of Vacuum Therapy—Vacusac, Timocki Medicinski Glasnik, Year XII, Zajecar, 1987, No. 1, pp. 77-82.

Arnljots et al., "Irrigation Treatment in Split-Thickness Skin Grafting of Intractable Leg Ulcers," Scandinavian Journal of Plastic and Reconstructive Surgery, 1985, vol. 19, pp. 211-213.

Article Excerpt, *Lancet*, Jun. 14, 1952, 1175-1176.

Article Excerpt: Part III. Resolving Selected Clinical Dilemmas, 17-20.

Arturson, M. Gosta, *The Pathophysiology of Severe Thermal Injury*, JBCR, 6(2): 129-146 (Mar.-Apr. 1985).

Ashrafov, A.A. and K.G. Ibishov, An Experimental and Clinical Validation for the Use of a Collagen Sponge for Treating the Suppurative-Inflammatory Complications of Wound Healing in Emergency Abdominal Surgery, *PubMed, Abs. Downloaded from Internet*, April.

Assessing the Patient with a Fistula or Draining Wounds, *Nursing*, Jun. 1980, 49-51.

Aubrey, D.A., et al., Treatment of the Perineal Wound after Proctectomy by Intermittent Irrigation, *Arch. Surg.*, Oct. 1984, 119, 1141-1144.

Author Unknown, "Wound Suction", Nursing, Oct. 1975, pp. 52-53, USA.

Avocat, C. et al., Nouvelle Presentation de Materiel Pour Drainage de Redon et Jost, *La Nouvelle Press Medicale*, Jun. 26, 1976, 5(6), 1644-1645 (in French).

Ayoub, M.H. and G. C. Bennet, A Study of Cutaneous and Intracompartmental Limb Pressures Associated with the Combined Use of Tourniquets and Plaster Casts, Abs., *Proc. and Reports of Univ., Colleges, Councils, Assoc., and Societies*, 68-8:3, May 1986, 497.

Bagautdinov, "Variant of External Vacuum Aspiration in the Treatment of Purulent Diseases of Soft Tissues," Current Problems in Modern Clinical Surgery, 1986, 4 pages.

(56) References Cited

OTHER PUBLICATIONS

Baldwin, J.F., Ed., The Columbus Medical Journal, Columbus, Ohio, 1887, V., 561.

Barbul, A., et al., Eds., Clinical and Experimental Approaches to Dermal and Epidermal Repair, Normal and Chronic Wounds, Progress in Clin. and Biol. Res., vol. 365, *Proc. of the 3rd Intnl. Symp. on Tissue Repair*, Miami, FL, Jan. 10-14, 1990, Abs.

Bar-El, Y. et al., Potentially dangerous Negative Intrapleural pressures Generated by Ordinary Pleural Drainage Systems, *Chest*, Feb. 2001, 119(2), 511-514.

Barker, D.E., et al., Vacuum Pack Technique of Temporary Abdominal Closure: A 7-Year Experience with 112 Patients, *Journ. of Trauma: Injury and Critical Care*, Feb. 2000, 4892), 201-207.

Bascom, J., Pilonidal Sinus, *Current Therapy in Colon and Rectal Surgery*, 1990, 1-8.

Benjamin, P.J., Faeculent Peritonitis: A Complication of Vacuum Drainage, *Br. J. Surg.*, 1980, 67, 453-454.

Berman and Fabiano, Closed Suction Drainage, *Orthopedics*, Mar. 1990, 13(3), 310-314.

Berman, A. T., et al., Comparison Between Intermittent (Spring-Loaded) and Continuous Closed Suction Drainage of Orthopedic Wounds: A Controlled Clinical Trial, *Orthopedics*, Mar. 1990, 13(3), 9 pgs.

Besst, J.A., Wound Healing—Intraoperative Factors, *Nursing Clinics of North America*, Dec. 1979, 14(4), 701-712.

Betancourt, Sergio, "A Method of Collecting the Effluent from Complicated Fistual of the Small Intestine," Dept. of Surgery, Allegheny General Hospital, Pittsburgh, p. 375, USA.

Biblehimer, Helen L., "Dealing With a Wound that Drains 1.5 Liters a Day," RN, Aug. 1986, pp. 21-23, USA.

Bier, A., Hyperemia as a Therapeutic Agent, Ed. Dr. Gustavus M. Blech, A. Robertson & Co., Chicago 1905, (the entire reference has been submitted, but pp. 74-85 may be the most relevant).

Birdsell, D.C., et al., The Theoretically Ideal Donor Site Dressing, *Gadgetry*, Div. of Plastic Surgery, Foothills, Hospital, Calgary, Canada, 535-537.

Bischoff, et al., Vacuum-Sealing Fixation of Mesh Grafts, *Euro. Journ. Plast. Surg.*, Jul. 2003, 26(4), 189-190, Abs. Downloaded from internet Apr. 6, 2006.

Bonnema, J., et al., A Prospective Randomized Trial of High Versus Low Vacuum Drainage after Axillary Dissection for Breast Cancer, *Amer. Journ. Surg.*, Feb. 1997, 173, 76-79.

Boretos, John W., "Cellular Polymers for Medical Use: The Vital Role of Porosity and Permeability," Cellular Polymers, 1984, vol. 3, pp. 345-358.

Britton, B.J., et al., A Comparison Between Disposable and Non-Disposable Suction Drainage Units: A Report of a Controlled Trial, *Br. J. Surg.* 1979, 66, 279-280.

Broader, J.H., et al., Management of the Pelvic Space after Proctectomy, *Br. J. Surg.*, 1974, 62, 94-97.

Brubacher, Lynda L., "To Heal a Draining Wound", RN, Mar. 1982, pp. 30-35, USA.

Brummelkamp, W.H., et al, "High-vacuum drainage and primary perineal wound closure in abdominoperineal excision of the rectum", The Netherlands Journal of Surgery, 1991 pp. 236-238, Netherlands.

Bruno, P., The Nature of Wound Healing: Implications for Nursing Practice, *Nursing Clinics of North American*, Dec. 1979, 14(4), 667-682.

Bucalo et al. "Inhibition of Cell Proliferation by Chronic Wound Fluid." Wound Repair and Regeneration. Miami, 1993. pp. 181-186.

Burdette-Taylor, S.R., Use of the Versatile One (V1) for Closed Suction Drainage to Stimulate Closure in Chronic Wounds in Home Care, Case Study Presentation, 2003, 2 pgs.

Bush, G.K., What is a Counter Irritant? Name Any That You Know and the Method of their Application, *Brit. Journ. Nurs.*, Oct. 1927, 232.

Calhoun, P. and K. Kenney, Pouching Management of Patients with Open abdomens, Eviscerations and Bowel Fistulas, Case Studies, *Univ. of Miami/Jackson Memorial Medical Center*, 1 page.

Candiani, P., et al., Repair of a Recurrent Urethrovaginal Fistula with an Island Bulbocavernous Musculocutaneous Flap, *Plastic and Reconstructive Surgery*, Dec. 1993, 1393-1394.

Carroll, P.L., The Principles of Vacuum and its Use in the Hospital Environment, 2nd Ed., 1986, 30p.

Chardak et al., "Experimental Studies on Synthetic Substitutes for Skin and Their Use in the Treatment of Burns," Annals of Surgery, 1962, vol. 155, No. 1, pp. 127-139.

Chariker, M.E., et al, "Effective Management of Incisional and Cutaneous Fistulae with Closed Suction Wound Drainage," Contemporary Surgery. Jun. 1989, pp. 59-63, vol. 34 USA.

Chart: Influence of Wound Closure on Healing of Perineal Wound after Abdominoperineal Resection or Total Proctocolectomy, excerpt faxed Jan. 23, 2006, 1 page.

Chua Patel, C.T., et al., Vacuum-Assisted Closure, *AJN*, Dec. 2000, 100(12), 45-49.

Cobb, J.P., Why Use Drains?, *Br. J. Bone Joint Surg.*, Nov. 1990, 72-B(6), 993-995.

Cooper, D.M., Optimizing Wound Healing, *Nursing Clinics of North America*, Mar. 1990, 25(1), 163-179.

Cooper, D.M., Postsurgical Nursing Intervention as an Adjunct to Wound Healing, *Nursing Clinics of North America*, Dec. 1979, 14(4), 713-726.

Cooper, S.M. and E. Young, Topical Negative Pressure, *Commentary, International Journal of Dermatology 2000*, 39, 892-898.

Costunchenok, B.M., et al., Effect of Vacuum on Surgical Purulent Wounds, *Vestnik Chirurgia 1986*, September, 18-20 (in Russian with English translation).

Cotton, P.B., et al., Early Endoscopy of Oesophagus, Stomach, and Duodenal Bulb in patients with Haematemesis and Melaena, *Br. Med. Journ.*, Jun. 1973, 2, 505-509.

Creative Medical Laboratories, Instruction Manual, Inc. P.O. Box 6347, Rochester, Minn. 55903. "TUGS" (Transportable Universal Gradient Suction), 8 pages.

Crisp, W.J. and A. Gunn, Granuflex Dressings for Closed Surgical Wounds Combined with Suction Drainage, *Annals of the Royal College of Surgeons of England*, 1990, 72, p. 76.

Cucuroos, Y.C., Vacuum Drainage of Post Operative Wounds, Kiev Army Hospital, Dept. of Hospital Surgery, Kiev medical University, 64-65 (in Russian with English translation).

Curtin, L.L., Wound Management: care and Cost—an Overview, *Nursing Management*, Feb. 1984, 15, 22-25.

Davidov et al. "Pathogenic Mechanism of the Effect of Vacuum Therapy on the Course of the Wound Process" Dec. 1986.

Davidov, Y.A., et al. Justifying the Usage of Force Early Secondary Sutures in treatment of Purulent Wounds by the Vacuum Therapy, *Vestnik Chirurgia 1990, March Edition*, 126-129 (in Russian with English translation).

Davidov, Y.A., et al., Concept of Clinico-Biological Management of Wound Process in Treatment of Purulent Wounds with the Help of Vacuum Therapy, *Vestnik Chirurgia 1991, February Edition*, 132-135 (in Russian with English translation).

Davidov, Y.A., et al., The Bacteriological & Cytological Assessment of Vacuum Therapy of Purulent Wounds, *Vestnik Chirurgia 1988, October Edition* 48-52 (in Russian with English translation). 1987.

Davidov, Y.A., et al., Vacuum Therapy in the Treatment of Purulent Lactational Mastitis, *Vestnik Chirurgia*, Grexova 1986, Sep. Edition, 66-70 (in Russian with English translation).

Davis, J.C. and T.K. Hunt, Eds., Problem Wounds: The Role of Oxygen, Chap. 1, Infection and Oxygen, 1988, 1-15.

Deknatel, Div. of Howmedica, Inc. Queens Village, NY 11429. "Pleur-evac.".

Dillon, Angiology, The Journal of Vascular Diseases, pp. 47-55, Jan. 1986, "Treatment of Resistant Venous Statis Ulcers and Dermatitis with the End-Diastolid Pneumatic Compression Boot."

Dilmaghani et al., "A Method for Closed Irrigation and Suction Therapy in Deep Wound Infections," Journal of Bone and Joint Surgery, 1969, vol. 51-A, No. 2, pp. 323-342.

Doillon, C.J., et al., Collagen-Based Wound Dressings: Control of the Pore Structure and Morphology, Journal of Biomedical Materials Research, Sep. 13, 2004, 20(8), 1219-1228. Abs. Downloaded from Internet http://www3.interscience.wiley.com, Apr. 28, 20.

(56) References Cited

OTHER PUBLICATIONS

Domkowski, P.W., et al., Evaluation of Vacuum-Assisted Closure in the Treatment of Poststernotomy Mediastinitis, *Journ. of Thorac. and Cardiovascular Surg.*, Aug. 2003, 126(2), 386-390.

Doss, Mirko, et al., Vacuum-Assisted Suction Drainage Versus Conventional Treatment in the Management of Poststernotomy Osteomyelitis, *Euro. Journ. Cardio-Thoracic. Surg.* 22 ((2002) 934-938.

Draper, J., Make the Dressing Fit the Wound, *Nursing Times*, Oct. 9, 1985, 32-35.

Dunbar, J.M., State What You Have Learned Recently on the Up-to-Date Care of Wounds, *Brit. Journ. Nurs.*, Dec. 1941, 200.

Dunlop, M.G, et al. Vacuum Drainage of Groin Wounds after Vascular Surgery: A Controled Trial, Br. J. Surg., May 1990, 77, 562-563.

Eaglstein, W.H., et al., Wound Dressings: Current and Future, *Clin. and Exper. Approaches to Dermal and Epidermal Repair: Normal and Chronic Wounds*, 1991, 257-265.

ECRI, Target Report, Negative Pressure Wound Therapy for Chronic Wounds, Jan. 24, 2006, 1-7, Downloaded from internet, http://www.target.ecri.org/summary/detail.aspx?dox_id=1155.

Eisenbud, D.E., Modern Wound Management, *Anadem Publishing*, Chap. 16, 109-116.

Ellingwood, F., Ellingwood's Therapeutist, Jun. 14, 1908, 2(6), 32-33.

Elwood, E.T., and D.G. Bolitho, Negative-Pressure Dressings in the Treatment of Hidradenitis Suppurative, *Annals of Plastic Surgery*, Jan. 2001, 46(1), 49-51.

Emerson, J.H. Emerson Co., 22 Cottage Park Ave., Cambridge, MA 02140, "Emerson Transport Suction Unit."

Engdahl, O. and J. Boe, Quantification of Aspirated Air Volume reduces Treatment Time in Pneumothorax, *Eur. Respir, J.*, 1990, 3, 649-652.

Engdahl, O., et al., Treatment of Pneumothorax: Application of a Technique which Quantifies Air Flow Through the Chest Drain, *Adv. in Therapy*, May/Jun. 1988, 5(3), 47-54.

Erichsen, J.E., Science and Art of Surgery, London: Longmans, Green, and Co., 1895, vol. 1, 258-259, and p. 289.

Fabian, T.S., The Evaluation of Subatmospheric Pressure and Hyperbaric Oxygen in Ischemic Full-Thickness Wound Healing, *Ischemic Full-Thickness Wound Healing*, Dec. 2000, 66(12), 1136-1143.

Falanga, Vincent, "Growth Factors and Chronic Wounds: The need to Understand the Microenvironment." Journal of Dermatology, vol. 19: 667-672, 1992.

Fay, M.F., Drainage Systems: Their Role in Wound Healing, *AORN Journal*, Sep. 1987, 46(3), 442-455.

Fellin, R., Managing Decubitus Ulcers, *Nursing Management*, Feb. 1984, 29-30.

Fingerhut, A., et al., Passive vs. Closed Suction drainage after Perineal Wound Closure Following Abdominoperineal Rectal Excision for Carcinoma, *Dis Colon Rectum*, Sep. 1995, 926-932.

Finley, John M., Practical Wound Management, pp. 45, 127, 143, 149, 207, 1981.

Firlit, C.F. and J.R. Canning, Surgical Wound Drainage: A Simple Device for Collection, *Journ. of Urology*, Aug. 1972, 108, p. 327.

Fisher, Jack, and R. W. Bert, Jr., A Technique for Skin Grafting Around Abdominal Wall Fistulas, *Annals of Plastic Surgery*, 11:6, Dec. 1983, 563-564.

Flanagan, et al., Optional Sump: Novel Use of Triple Lumen Closed Drainage System, *Anz. J. Surg.*, Nov. 2002, 72(11), 806-807, Abs. Downloaded from internet Nov. 30, 2003.

Fleck, C.A., When Negative is Positive: A Review of Negative Pressure Wound therapy, *Wound Care*, Mar./Apr. 2004, 20-25.

Fleischmann, "Vacuum sealing: indication, technique, and results," *European Journal of Orthopaedic Surgery & Traumatology*, vol. 5(1), 1995, pp. 37-40.

Fleischmann, W. Acta Orthopaedical Belgica, "Treatment of Bone and Soft Tissue Defects in Infected Nonunion," vol. 58, *Suppl. I—1992*, pp. 227-235.

Fleischmann, W. Unfall Chirurg, Springer-Variag, "Vakuumversiegelung zur Behandlung des Weichteilschadens bei offenen Frakturen," (English abstract, no English translation), 1993, pp. 488-492.

Fleischmann, W. Wund Forum Spezia!, "Vakuumversiegelung zur Behandlung von Problemwunden" (with English translation: Vacuum Sealing for Treatment of Problematical Wounds), *IHW '94*, 6 pages.

Flynn, M.E. and D.T. Rovee, Wound Healing Mechanisms, *Amer. Journ. of Nursing*, Oct. 1982, 1544-1556.

Froberg, Birgitta et al., Vacusac Therapy—A Supplement to the Treatment of Varicose Ulcers? (Stockholm) 1990 37 pages.

Garcia-Rinaldi, R., et al., Improving the Efficiency of Wound Drainage Catheters, *Amer. Journ. of Surg.*, Sep. 1975, 130, 372-373.

Geiger Jones, E., et al., Management of an Iliostomy and Mucous Fistula Located in a Dehisced Wound in a Patient with Morbid Obesity, *J. WOCN*, Nov. 2003, 30(6), 351-356.

Gill, P., What is a Counter-Irritant? Name Three and the Method of Applying them, *Brit. Journ. Nurs.*, Jun. 1934, 142.

Goddard, L., Inflammation: Its Cause and Treatment, *Brit. Journ. Nurs.*, Jan. 1944, 2.

Gogia, Prem P., "The Biology of Wound Healing." Ostomy/ Wound Management. Nov.-Dec. 1992, pp. 12-20.

Gomco Suction Equipment & Accessories Guide, Catalog, Apr. 2006, 20 pages.

Gouttefangeas, C. et al., Functional T Lymphocytes Infiltrate Implanted Polyvinyl Alcohol Foams During Surgical Wound Closure Therapy, *Clin. Exp. Immunol. 2001*, 124, 398-405.

Grabowski, S., Leczenie ran z zastosowaniem posicnienia (wg Redona I Josta), *Il Klinik Xhieuefxnej AM w Warszawie; klerownik: Prof. Dr. Z. Lapinski*, No. 1, 19-21 (in Polish).

Grishdevich, V. and N. Ostrovsky, Postburn Facial Resurfacing with a Split Ascending Neck Flap, *Plastic and Reconstructive Surgery*, Dec. 1993, 1384-1391.

Grobmyer, et al., High-Pressure Gradients Generated by Closed-Suction Surgical Drainage Systems, *Surg. Infect. (Larchmt)*, Autumn 2002, 3(3), 245-249, Abs., Downloaded Nov. 30, 2003.

Grover, R. and R. Sanders, Recent Advances: Plastic Surgery, Clinical Review, *BMJ*, Aug. 8, 1998, 317, 397-400.

Gupta, S., Ed., Guidelines for Managing pressure Ulcers with Negative Pressure Wound Therapy, *Advances in Skin & Wound Care Suppl.*, Nov./Dec. 2004, 17(2), 1-16.

Gupta, S., Guidelines for Managing: Pressure Ulcers with Negative Pressure Wound Therapy, Downloaded from internet http://proquest.umi.com on Feb. 3, 2006. 19 pages.

Gwan-Nulla, D.N. and R.S. Casal, Toxic Shock Syndrome Associated with the Use of the Vacuum-Assisted Closure Device, *Ann. Plast. Surg.*, Nov. 2001, 47(5), 552-554.

Hallstrom, B.R. and J.F. Steele, Postoperative Course after Total Hip Arthroplasty: Wound Drainage versus No Drainage, *Orthopaedic Review*, Jul. 1992, 847-851.

Hanbok för Hälso-Och Sjukvardsarbete Lokal Anvisning för Landstinget Sörmland, Jan. 2001, 7 pgs, (in Swedish), Downloaded from Internet http://www.landstinget.sormland.se, Aug. 14, 2001, 7 pages.

Hargens et al., Aviation, Space and Environmental medicine, pp. 934-937, Oct. 1991, "Lower Body Negative Pressure to Provide Load Bearing in Space."

Hargens et al., Space Physiology Laboratory, Life Science Division, NASA Ames Research Center, "Control of Circulatory Functions in Altered Gravitational Fields."

Harkiss, K., Cheaper in the Long Run, *Community Outlook*, Aug. 1985, 19-22.

Harle, A. Z. Orthop., 127: 513-517 (1989), "Schwachstellen herkommlicher Drainagen."

Hartz, R.S., et al., Healing of the Perineal Wound, *Arch. Surg.*, Apr. 1980, 115, 471-474.

Harvard Pilgrim Health Care, Technology Assessment Policy, TA 6.29 Negative Pressure Wound therapy for Wound Healing, Dec. 2004, 1-6.

Hay, J., et al., Management of the Pelvic Space With or Without Omentoplasty after Abdominoperineal Resection for Carcinoma of the Rectum: a Prospective Multicenter Study, *Eur. J. Surg*, 1997, Abs.

(56) References Cited

OTHER PUBLICATIONS

Higgins, S., The Effectiveness of Vacuum Assisted Closure (VAC) in Wound Healing, *Centre for Clinical Effectiveness, Monash Medical Centre*, Clayton VIC Australia, Dec. 2003, 1-16.

Hilsabeck, J.R., The Presacral Space as a Collector of Fluid Accumulations Following Rectal Anastomosis: Tolerance of Rectal Anastomosis to Closed Suction Pelvic Drainage, *Amer. Soc. of Colon and Rectal Surgeons*, Oct., 25(7), 680-684.

Hilton, P., Surgical Wound Drainage: A Survey of Practices among Gynaecologists in the British Isles, *Br. Journ. of Obstetrics and Gynaecology*, Oct. 1988, 95, 1063-1069.

Hollis, H.W. and M.R. Troy, A Practical Approach to Wound care in patients with Complex Enterocutaneous Fistulas, *Surg., Gyn. & Obs.*, Aug. 1985, 161, 179-181.

Hugh, T.B., Abdominal Wound Drainage, *Med. Journ. of Australia*, May 4, 1987, 146, p. 505 (Correspondence).

Hulten, L., et al., Primary Closure of Perineal Wound after Proctocolectomy or Rectal Excision, *Acta Chir. Scand.*, 1971, 137, 467-469.

Hunt, T.K. and J.E. Dunphy, Eds., Fundamentals of Wound Management, *Appleton-Century-Crofts/New York*, 416-447.

Hyperemia by Suction Apparatus, Chapter VIII, 74-85.

Ilizarov, G.A., The Tension-Stress Effect on the Genesis and Growth of Tissues: Part II., *Clinical Orthopaedics and Related Research*, Feb. 1989, 239, 263-283.

Izmailov, S.G., et al., Device for Treatment of wounds and Abdominal Cavity, Contents, Surg. No. 8 1997, Downloaded from internet http://www.mediasphera.ru/surgery/97/8/e8-97ref.htm.

Izmailov, S.G., The Treatment of Eventrations with a Special Apparatus, Abstracts, Surg. No. 1 1997, Downloaded from internet, http://www.mediasphera.ru/surgery/97/1/el-97ref.htm.

Jeter, K., Closed Suction Wound Drainage System, *J. WOCN*, Mar./Apr. 2004, 51 (correspondence).

Jeter, Katherine F. ET, Managing Draining Wounds and Fistulae: New and Established Methods, Chronic Wound Care, Chapter 27, pp. 240-246, 1990.

Johnson, F.E., An Improved Technique for Skin Graft Placement using a Suction Drain, *Surgery, Gynecology & Obstetrics*, Dec. 1984, 159(6), 584-585.

Kazan Medical Institute Doctors, A Gadget to Bring the Wound Edges Close, 78-79 (in Russian with English translation). Aug. 20, 1985.

KCI, Inc., If It's Not V.A.C. Therapy, It's Not Negative Pressure Wound Therapy, *KCI Brochure*, Jan. 2005, 1-5.

KCI, Inc., Introducing the V.A.C. GranuFoam Silver Dressing, *Flyer*, 2 pages.

KCI, Inc., The V.A.C. System, 2000-2001, Brochure, 2 pgs.

KCI, Inc., Vacuum Assisted Closure (VAC) from Wound Healing, *Evidence Note 5, NHS Quality Improvement Scotland*, Nov. 2003, 1 page.

Keen, W.W., Ed., Surgery, Its Principles and Practice, 1919, W. B. Saunders Company, p. 56, excerpt.

Keith, C.F., Wound management Following Head and Neck Surgery, *Nursing Clinics of North America*, Dec. 1979, 14(4) 761-779.

Kennard, H.W., Bier's Hyperaemia, *Brit. Journ. Nurs.*, Mar. 20, 1909, 223.

Khil'Kin, A.M., Use of a Collagen Hemostatic Sponge for the Experimental Closing of the Surface of a Liver Wound (article in Russian), Citation Downloaded from internet http://www.ncbi.nlm.nih.gov Apr. 24, 2006.

Kim, S.H., et al., Wangensteen Suction Drainage, apparatus in Neurosurgical Practice, *Dept. of Neurosurgery, Yonsei University of College of Medicine*, Seoul, Korea, 1975, 159-160, Abs. (in Korean and Abstract in English).

Kloth, L.C. and J.M. McCulloch, Wound Healing Alternatives in Management, 3rd Ed., Chap. 10, 339-352.

Knight, Marie Ray, A Second Skin for Patients with Large Draining Wounds, Nursing, Jan. 1976, p. 37, USA.

Kohlman, Phyllis A., et al, "Pouching Procedure to Collect Drainage From Around a Biliary Drainage Catheter," Ostomy/Wound Management, Nov./Dec. 1991, pp. 47-50, vol. 37.

Kordasiewicz, L.M., Abdominal Wound with a Fistula and Large Amount of Drainage Status after Incarcerate Hernia Repair, *J. WOCN*, May/Jun. 2004, 31(3), 150-153.

Kremlin Papers, A Collection of Published Studies Complementing the Research and Innovation of Wound Care, from *Vestnik Khirurgii, BlueSky Publishing, A Div. of BlueSky Medical Group Inc.*, 2004. 17 pages.

Landes, R.R. and I. Melnick, An Improved Suction Device for Draining Wounds, Arch. Surg., May 1972, 104, p. 707.

Landis, E.M. and J.H. Gibbon, Jr., The Effects of Alternate Suction and Pressure on Blood Flow to the Lower Extremities, Alternate Suction and Pressure, 925-961.

Larichev, A.B., Vacuum Therapy of Wounds and Wound Infection, *1st. Ed., BlueSky Publishing*, 2005.237 pgs.

Lee, J.H. and H.J. Yang, Application of Medifoam B® & Negative Pressure Therapy for the Auxiliary Treatment of Pressure Sore, *Dept. Plastic and Reconstructive Surg.*, College of Medicine, Eulji Univ., Daejeon, Korea, Abs. Sep. 31, 2004, 1 page.

Lehrman, "The Not-So-Bald-Truth," Science, Sep. 1992, p. 42.

Letsou et al. "Stimulation of Adenylate Cyclase Activity in Cultured Endothelial Cells Subjected to Cyclic Stretch." Cardiovascular Surgery 3. Toronto. Sep. 1989, pp. 634-639.

Linden van der, Willem, Randomized Trial of Drainage After Cholecystectomy, Modern Operative Techniques, Voluje 141, Feb. 1981, pp. 289-294.

Lockwood, C.B., Aseptic Surgery, Drainage, *Brit. Journ. Nurs.*, Mar. 26, 1904, 245.

Luchette, F.A., When Should the General Surgeon Leave the Abdomen Open?, Division of Trauma, Surgical Critical Care and Burns, Loyola University Medical Center, Maywood, Illinois., 37 pages (date N/A).

Lumley, J.S.P., et al., The Physical and bacteriological Properties of Disposable and Non-Disposable Suction Drainage Units in the Laboratory, *Br. J. Surg.*, 1974, 61, 832-837.

Lundvall, J. and T. Lanne, Transmission of Externally applied Negative pressure to the Underlying Tissue: A Study on the Upper Arm of Man, *Acta Physiol. Scand. 1989*, 136, 403-409.

Maddin et al., International Journal of Dermatology, 29: 446-450 (1990), "The Biological Effects of a Pulsed Electrostatic Field with Specific References to Hair: Electrotrichogenesis."

Magee, C., et al., Potentiation of Wound Infection by Surgical Drains, *Amer. Journ. of Surg.*, May 1976, 131, 547-549.

Maitland and Mathieson, Suction Drainage, *Brit. J. Surg.*, Mar. 1970, 57(3), 195-197.

Mayo, C.W., The One-Stage Combined Abdominoperineal Resection for Carcinoma of the Rectum, RectoSigmoid and Sigmoid, *Surgical Clinics of North America*, Aug. 1939, Mayo Clinic Number, 1011-1012.

McFarlane, R.M., The Use of Continuous Suction under Skin Flaps, *Br. Journ. Plast. Surg.*, 77-86.

McGuire, S., Drainage after Abdominal Section, *Br. Journ. of Nurs.*, Dec. 15, 1903, 447-449.

McLaughlan, James, Sterile Microenvironment for Postoperative Wound Care, The Lancet, pp. 503-504, Sep. 2, 1978.

Medela, Inc., Pleupump MK II, Aug. 14, 2001, Brochure (in German). 12 pages.

Mendez-Eastman, S., Guidelines for Using Negative Pressure Wound Therapy, Advances in Skin & Wound Care, 14(6), Nov./Dec. 2001, 314-325.

Mendez-Eastman, S., When Wounds Won't Heal, *RN*, Jan. 1998, 2-7.

Meyer and Schmieden, Bier's Hyperemic Treatment, Fig. 69-70, 557.

Meyer and Schmieden, Bier's Hyperemic Treatment, Published 1908 W. B. Saunders Company, 44-65.

Meyer, W. & Schmieden, V., Bier's Hyperemic Treatment, W B. Saunders Company 1908, (the entire reference has been submitted, but pp. 44-65 may be the most relevant).

Microtek Heritage, Inc. P.O. Box 2487, Columbus, MS 39704, "Wound-Evac ET," 4 pages.

(56) References Cited

OTHER PUBLICATIONS

Miles, W. Ernest, "Technique of the Radical Operation for Cancer of the Rectum", The British Journal of Surgery, pp. 292-304, United Kingdom 1914-1915.
Miles, W.E., A Method of Performing Abdominoperineal Excision for Carcinoma of the Rectum and of the Terminal Portion of the Pelvic Colon, *The Lancet*, Dec. 19, 1908, 1812-1813.
Miller, M.S. and C. McDaniel, Treating a Pilonidal Cystectomy Abscess Wound with the BlueSky Medical Versatile 1™ Negative Pressure Wound Therapy, *The Wound Healing Center*, Terre Haute, Indiana, Case Study 2004-2006, 1 page.
Moloney, G.E., Apposition and Drainage of Large Skin Flaps by Suction, *Australian and New Zealand Journ. of Surg.*, 173-179—1950's.
Morykwas, M.J., et al., Effects of Varying Levels of Subatmospheric Pressure on the Rate of Granulation Tissue Formation in Experimental Wounds in Swine, *Abs., Ann. Plast. Surg. 2001*, 47: 547.
Moserova, J. and E. Houskova, The Healing and Treatment of Skin Defects, 1989, 116-143.
Moss, W., What is Cellulitis? Describe Some Forms of Treatment You Would Expect to be Used for Cellulitis of the Arm, *Brit. Journ. Nurs.*, Nov. 1935, 282.
Mulder, G.D., Ed., et al., Clinicians' Pocket Guide to Chronic Wound Repair, *Wound Healing Publications*, Spartanburg, SC, 1991, 54-55.
Mullner, T., et al., The Use of Negative Pressue to Promote the Healing of Tissue Defects: A Clinical Trial Using the Vacuum Sealing Technique, *Br. J. Plast. Surg.*, Apr. 1997, 51(1), 79, Abs.
Musashaikhov, K.T., et al., The Course of Wound Healing under the Influence of Polyphepan in patients with Diabetes Mellitus, Abstracts, Surg. No. 5, 1997, Downloaded from internet, http://www.mediasphera.ru/surgery/97/5/e5-97ref.htm, 1 page.
Nakayama et al., Ann. Plast. Surg., 26: 499-502 (1991), "A New Dressing Method for Free Skin Grafting in Hands."
Nakayama, Y., et al., "A New Method for the Dressing of Free Skin Grafts", Plastic and Reconstructive Surgery, Dec. 1990 pp. 1216-1219, UK.
Nasser, A.N., The Use of the Mini-Flap Wound Suction Drain in maxillofacial Surgery, *Annals of the Royal College of Surgeons of England*, 1986, 68, 151-153.
Navsaria, P.H., et al., Temporary Closure of Open Abdominal Wounds by the Modified Sandwich-Vacuum Pack Technique, *Br. Journ. Surg.*, 2003, 90, 718-722.
Nghiem, D.D., A Technique of Catheter insertion for Uncomplicated Peritoneal Dialysis, *Surgery, Gynecology & Obstetrics*, Dec. 1983, 157, 575-576.
Nicholas, J.M., Options for Management of the Open Abdomen, Presentation from Emory University School of Medicine, 66 pgs.
Nightingale, K., Making Sense of wound Drainage, *Nursing time* Jul. 5, 1989, 85(27), 40-42.
Noblett, E.A., What is an Empyema? What Operations are Undertaken for its Relief, and What Have You to Say About the After-Nursing?, *Brit. Journ. Nurs.*, Apr. 29, 1916, 375.
NURSING75, Wound Suction: Better Drainage with Fewer Problems, Oct., 52-53.
O'Byrne, C., Clinical Detection and Management of Postoperative Wound Sepsis, *Nursing Clinics of North American*, Dec. 1979, 14(4), 727-741.
Ohotskii, V.P., et al., Usage of Vacuum Suction During the Primary Surgical Debridement of Open Limb Injuries, *Sovetskaya Medicina*, Jan. 17-20, 1973 (in Russian with English translation).
Olenius et al., "Mitotic Activity in Expanded Human Skin." Plastic and Reconstructive Surgery. Feb. 1993. 213-215.
Ontario Ministry of Health and Long Term Care for the Ontario Health Technology Advisory Committee, "Vacuum Assisted Closure Therapy for Wound Care, Health Technology Literature Review," Dec. 2004, Toronto, Ontario, Canada, pp. 1-57.
Orgill, D. P., et al., Microdeformational Wound Therapy—A New Era in Wound Healing, *Tissue Engin. and Wound Healing Laboratory*, Brigham and Women's Hospital, Business Briefing: Global Surgery—Future Direction 2005, 22.

Orgill, D., et al., Current Concepts and Approaches to Wound Healing, *Critical Care Medicine*, Sep. 1988, 16(9), 899-908.
Orgill, D.P., et al., Guidelines for Treatment of Complex Chest Wounds with Negative Pressure Wound Therapy, *Wounds, A Compendium of Clinical Research and Practice*, Suppl. B, Dec. 2004, 1-23.
Oschsner, A.J., Surgical Diagnosis and Treatment, 1921, 11, 266-269.
Parker, M.J. and C. Roberts, Closed suction Surgical Wound Drainage after Orthopaedic Surgery, *Cochran Database of Systematic Review 2005*, 3, 3 pages.
Pham, C., et al., Vacuum-Assisted Closure for the Management of Wounds: An Accelerated Systematic Review, *Asemip—Accelerated Review of Vacuum Assisted Wound Closure*, Report No. 27, Dec. 2003, 1-52.
Precision Medical, Power VAC+ Intermittent Aspirator, http://precisionmedical.com Downloaded from internet Apr. 10, 2006, 2 pages.
Putney F. Johnson, "The Use of Continuous Negative Pressure after Laryngectomy and Radical Neck Dissection", Surgery, Gynecology & Obstetrics, Aug. 1956, pp. 244-246, USA.
Raffl, Arthur B., "Use of Negative Pressure Under Skin Flaps After Radical Mastectomy,"Dept. of Surgery, State Univ. of N.Y., College of Medicine, Syracuse, NY, Submitted for publication Apr. 1953, p. 1048, USA.
Ramirez, O.M., et al., Optimal Wound Healing under Op-Site Dressing, Ideas and Innovations, 73(3), pp. 474-475.
Rammensee, H.G., Untersuchung der Lymphozytenin filtrate in Implantierte PVA-Schwämme nach der Therapie infizierter Wunden mit Vakuumversiegelung, Aus dem Interfakulatären Institut für Zellbiologie der Universität Tübingen Abeilung Immunologie Abteilungsl.
Ranson, John H. M.D., Safer Intraperitoneal Sump Drainage, Surgery Gynnecology and Obstetrics, pp. 841-842, 1973 vol. 137.
Redon, H. and J. Troques, La Fermeture Sous Depression des Plaies Etendues, *Academe de Chirurgie*, Mar. 1954, 304-306. (in French).
Redon, H., Closure of Large Wounds under a Partial Vacuum, Paris, *Notes on Practical Medicine*, published under L. Rouques, 1-3.
Reedy, J., The Science Behind Wound Healing, *UW Health Sciences/ UW Medicine News and Community Relations*, Winter/Spring 2005, 4 pages.
Reference Handbook of the Medical Sciences, *Hyperaemia*, 553.
Reid, Daniel P., Information on Cupping or Using Suction Cups on Wounds and for Healing Purposes, *Chinese Herbal Medicine*, 2 pages.
Reimann, D., et al., Successful Treatment Due to Vacuum Seal Technique of a Severe Scedosporium Apiospermum Skin Infection in a Renal Transplant Recipient, *Nephrol. Dial. Transplant*, 2004, 19 (1), 245-248.
Richter, Treatment of Inflammatory Conditions of the Skin with Hot Baths, *Brit. Journ. Nurs.*, Aug. 25, 1906, 149.
Roberts, R.H., et al., Randomised Trial of Medinorm LVS and Surgivac Drainage System after Operations for Breast Cancer May 1999, *Amer. Journ. Surg.*, Feb. 1997, 2 pgs.
Rodrigo, J.J., et al., The Effect of Varying Degrees of Suction Pressure on Drainage of Hematomas, *Dept. of Orthopaedic Surgery*, University of California, David, Sacramento, California, 9 pages (date N/A).
Rosser, C.J., et al., A New Technique to Manage Perineal Wounds, *Infections in Urology*, Mar./Apr. 2000, 4 pgs.
Royle, G.T. and B.J. Britton, Disposable Drains, *Articles of the Royal College of Surgeons of England*, (1984), vol. 66, 1 page.
Russ and Fleischmann, Vakuumversiegelung, List of References (in English and German), 2000, 4 pgs.
Sagi, A., Burn Hazard from Cupping—An Ancient Universal Medication Still in Practice, *bums*, 1988, 14(4), 323-325.
Sames, C.P., Sealing of Wounds with Vacuum Drainage, *Br. Med. Journ.*, Nov. 5, 1977, p. 1223, Correspondence.
Samson, D., et al., Wound-Healing Technologies: Low-Level Laser and Vacuum-Assisted Closure, *Evidence report/Technology Assessment*, No. 111, Dec. 2004, ARHQ Publication No. 05-E005-2 97 pages.

(56) References Cited

OTHER PUBLICATIONS

Sandahl, L., Slides at Geisinger Medical Center, Danville, PA, Apr. 10, 1990, Correspondence, 4 pages.
Schaffer, D.B., Closed Suction Wound Drainage, Nursing97, Nov., Downloaded from internet www.springnet.com, 62-64. 1997.
Schein et al., "The 'Sandwich Technique' in the Management of the Open Abdomen," British Journal of Surger, 1986, vol. 73, May, pp. 369-370.
Schumann, D., Preoperative Measures to Promote Wound Healing, *Nursing Clinics of North America*, Dec. 1979, 14(4), 683-699.
Schwab, Peter M. and Kelly, Keith A., "Primary closure of the Perineal Wound After Proctectomy,"Mayo Clinic Proc., Mar. 1974, pp. 176-179, vol. 49, US.
Scott, F., Babies in Bottles, *Advance for Resp. Care Practitioners*, Nov. 23, 1992, 2 pgs.
Senyutovich, R.V., Napkin Preventing Abdominal Contamination in Performance of Colonic Anastomosis, Abstracts, Downloaded from internet, http://www.mediasphera.ru/ surgery/97/1/el-97ref.htm— 1997, 1 page.
Shaer, W.D., et al., Inexpensive Vacuum-Assisted Closure Employing a Conventional Disposable Closed-Suction Drainage System, *Plastic and Reconstructive Surgery*, Jan. 2001, 292.
Sheen, A.W., Some Experiences of Shell Wounds in the Present War, (excerpt), *Brit. Journ. Nurs.*, Jan. 16, 1915, 42.
Sheppard, M.D., "Sealed Drainage of Wounds", The Lancet, Jun. 14, 1952, pp. 1174-1176.
Smith, L.A., et al., Vacuum Pack Technique of Temporary Abdominal Closure: A Four-Year Experience, *Amer. Surg.*, Dec. 1997, 63(12), 1102-1108.
Spahn, Slide presented at the WOCN meeting in Ontario, California, Sep. 2001.
Sparta Instrument Corp. 26602 Corporate Ave., Hayward, CA 94545, Power Source Multi-Purpose Surgical Aspirator, 1 page.
Specific Inflammations, Diseases of the Skin, 549-550.
Spengler, Michael D., el al, "Performance of Filtered Sump Wound Drainage Tubes", Surgery, Gynecology & Obstetrics, Mar. 1982, pp. 333-336, vol. 54, USA.
Stewart, M. F., et al., Cleaning v Healing, *Community Outlook*, Aug. 1985, 22-26.
Surgidyne, Closed Systems for Management of Wound Drainage, Brochure and Catalog, Downloaded from internet, www.sterion.com, 6 pages (date N/A).
Svedman, P., A Dressing Allowing Continuous Treatment of a Biosurface, *IRCS Med. Science: Biomed. Tech.; Clinic. Med.; Surg. and Transplantation*, 1979, 7, p. 221.
Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.
Swanson, L., Solving Stubborn-Wound problem Could Save Millions, Team Says, *JAMC, 23 FEVR*, 1999: 160(4), p. 556.
Taylor, Virginia, Meeting the Challenge of Fistulas & Draining Wounds, Nursing, Jun. 1980, pp. 45-51, USA.
Techno Takatsuki Co., Ltd., 8-16 Hatchonishimachi, Takatsuki City, Osaka, Japan, "HiBlow Air Pump."
Tennant, C.E., "The Use of Hyperemia in the Postoperative Treatment of Lesions of the Extremities and Thorax," Jour. A. M. A., May 8, 1915, pp. 1548-1549.
Tenta, L.T., et al., Suction Drainage of Wounds of the Head and Neck, *Surg. Gyn. & Ob.*, Dec. 1989, 169, p. 558.
The Bier Treatment, *Brit. Journ. Nurs.*, Jun. 6, 1908, 452.
The British Journal of Nursing, Nov. 4, 1911, 368.
Tittel, K. and G. Tolksdorff, Forum: VariDyne—Neue Standard in der Postoperative Wunddrainage (New Standards in Postoperative Wound Drainage), *Unfallchirurgie*, 1988 14(2), 104-107 (in German with English Translation).
Tribble, David E. M.D., An Improved Sump Drain-Irrigation Device of Simple Construction, Archives of Surgery New York, pp. 511-513, 1972 vol. 105.
Tuberculous Joints, *Nursing record & Hospital World*, Apr. 28, 1894, 280.

Unknown, "The RN Magazine/University of California Continuing Education Curriculum; Examination on 'To heal a draining wound'", RN, Mar. 1982, p. 36, USA.
NURSING75, Wound Suction, Nursing75, Oct., pp. 52-53.
Unknown, "Pleupump MK II is the new micro-data controlled thoracic drainage", http://www.xenamedical.se/pleu_sug.htm, Aug. 14, 2001.
Urschel, J.D., et al., The Effect of Mechanical Stress on Soft and Hard Tissue Repair; A Review, *Br. Journ. Plast. Surg.*, 1988, 41, 182-186.
Usypov, Y. N. and M.V. Ephfanov, Active Drainage of wounds, Dept. of Hospital Surgery, Army Medical Academy, Leningrad, *Vestnik Chirurgia 1987, April Edition*, 42-45 (in Russian with English translation).
Valenta, A.L., Using the Vacuum Dressing Alternative for Difficult Wounds, *AIN*, Apr. 1994, 44-45.
Van Heurn, L.W.E. and P.R.G. Brink, Prospective Randomized Trial of High versus Low Vacuum Drainage after Axillary Lymphadenectomy, *Br. Journ. Surg. 1995*, 82, 931-932.
Van Way III, C.W. Prevention of Suction-Induced Gastric mucosal damage in Dogs, *Critical Care Medicine*, Aug. 1987, 15(8), 774-777.
Varley, G.W. and S.A. Milner, Wound Drains in Proximal Femoral Fracture Surgery: A Randomized prospective Trial of 177 Patients, *J. R. Coll. Surg. Edinb.*, Dec. 1995, 40, 416-418.
Vijanto, J. and J. Raekallio, Local Hyperalimentation of Open Wounds, *Br. J. Surg.*, 1976, 63, 427-430.
Wackenfors, A., et al., Effects of Vacuum-Assisted Closure Therapy on Inguinal Wound Edge Microvascular Blood Flow, *Wound Rep. Reg*, 2004, 12, 600-606.
Warren, J.C. and A.P. Gould, Ed., The International Text-Book of Surgery, 1902, 1, 70-79.
Waymck, J.P., et al., An Evaluation of Aquaphor Gauze Dressing in Burned children, Abs.
Wayne, M.A., Cook Pneumothorax Catheter Set, Wayne Pneumothorax Catheter Set, *Cook Critical Care*, Cook Incorporated 1997, 3 pgs.
Wells Johnson Company, 2045 N. Forbes Blvd., Suite 106, Tuscon, AZ. Point 5 Aspirator, 1 page.
Westaby, S., Wound Care No. 11, *Nursing Times*, Jul. 21, 1982, 41-48.
White, R.A., et al., Vacuum-Assisted Closure Complicated by Erosion and Hemorrhage of the Anterior Tibial Artery, Journal of Orthopaedic Trauma, Jan. 2005, 19(1), 56-59, Abs. BlueSky internal email dtd. Nov. 9, 2005.
Williams, et al., Survey of the Use of Suction Drains in head and Neck Surgery and Analysis of Their Biomechanical Properties, *J. Otolaryngol.*, Feb. 2003, 32(1), 16-22, Abs. Downloaded from Internet Nov. 30, 2003.
Windows on Medical Technology, Vacuum-Assisted Wound Closure for Chronic and Acute Wounds, *ECRI Health Technology Assessment Information Service*, Oct. 2000, 38, 1-21.
Witkowski, J.A. and Parish, L.C., Synthetic Dressings: Wound Healing in the '80s, *Hospital Therapy*, Nov. 1986, 75-84.
Wolthuis, Roger A., et al, "Physiological Effects of Locally Applied Reduced Pressure in Man," Physiological Reviews, Jul. 1974, pp. 566-595 vol. 54, No. 3, USA.
Wooding-Scott, Margaret, et.al, "No Wound is Too Big for Resourceful Nurses," RN, Dec. 1988, pp. 22-25, USA.
Worth, M.H. and H.W. Andersen, The Effectiveness of Bacterial Filtration in Vented Wound Drains, *Journ. of Surg. Research*, 1979, 27, 405-407.
Wu, P., et al., In Vitro Assessment of Water Vapour Transmission of Synthetic Wound Dressings, *Biomaterials*, 1995, 16(3), 171-175.
Wu W.S., et al. Vacuum therapy as an intermediate phase in wound closure: a clinical experience, Eur J Past Surg (2000) 23: 174-177.
Wysocki et al., "Wound Fluid form Chronic Leg Ulcers Contains Elevated Levels of Metalloproteinases MMP-2 and MMP-9." The Society for Investigative Dermatology, Inc. Jul. 1993. 64-68.
Yukhtin, V.I., et al., Surgical Treatment of Purulent Diseases of Soft tissues and Bones with the Use of Drainage-Bathing System, Content, Surg. No. 9 1997, Downloaded from internet, http://www.mediasphera.ru/surgery/97/9/e9-97ref.htm, 1 page.

(56) References Cited

OTHER PUBLICATIONS

Zamierowski, David S., Letter:"All Foam Sponges are not Equal in Vacuum Dressings," British Journal of Plastic Surgery, 1999, 52, 78-81, p. 79, United Kingdom.

Zhetimkarimov, D.S. and V.K. Ostrovsky, The Applied Significance of Anatomic Pecularities of Greater Momentum, CONTENTS, Surg. No. 6, 1997, Downloaded from internet http://www.mediasphera.ru/surgery/97/6/e6-97ref.htm, 1 page.

Zivadinovic, Gorica, Veljko Dukic, and Sava Filipovic, Our Experience in the Treatment of Patients with Arterial Failure of the Extremities Using the Vacusac Unit, Timocki Medicinski Glasnik, Year XII, Zajecar, 1987 No. 1, pp. 55-65.

Zivadinovic, Gorica, Veljko Dukic, Zivan Maksimovic, Dorde Radak and Predrag Pesko, Vacuum Therapy in the Treatment of Peripheral Blood Vessels, Timocki Medicinski Glasnik (Conference Papers of the 5th Timok Medical Days, Majdanepek, 1986), Year XI, Zajec.

\* cited by examiner

ENCLOSURE-BASED REDUCED PRESSURE TREATMENT SYSTEM

CLAIM OF PRIORITY

This application is a divisional of U.S. application Ser. No. 11/075,020, filed on Mar. 8, 2005, and which claims the benefit of U.S. provisional application No. 60/551,951, filed on Mar. 9, 2004. The full disclosures of these applications are incorporated herein by reference.

BACKGROUND OF THE INVENTION

Field of the Invention

The present invention generally relates to treatment of wounds and other infirmities and conditions, and more specifically to an improved apparatus and method for treating a portion of a patient's body by applying reduced pressure to the portion of the body for which treatment is desired. In this context, the terms "wound," "infirmity," "condition" and "body" are to be interpreted broadly, to include any body part of a patient that may be treated using reduced pressure.

The treatment of open or chronic wounds that are too large to spontaneously close or otherwise fail to heal by means of applying reduced pressure to the site of the wound is well known in the art. One such system is disclosed in U.S. patent application Ser. No. 10/652,100, which was filed by one of the present inventors with the U.S. Patent and Trademark Office on Aug. 28, 2003. The disclosure of this U.S. patent application is incorporated herein by reference. Another system is disclosed in U.S. patent application Ser. No. 11/026,733, entitled "Improved Reduced Pressure Wound Treatment Appliance," which was filed by one of the present inventors with the U.S. Patent and Trademark Office on Dec. 30, 2004. The disclosure of this U.S. patent application is also incorporated herein by reference. Yet another system is disclosed in a U.S. patent application entitled "Improved Flexible Reduced Pressure Wound Treatment Appliance," which was filed by the present inventor with the U.S. Patent and Trademark Office on or about Feb. 24, 2005. The disclosure of this U.S. patent application is also incorporated herein by reference.

Reduced pressure wound treatment systems currently known in the art commonly involve placing a cover that is impermeable to liquids over the wound, using various means to seal the cover to the tissue of the patient surrounding the wound, and connecting a source of reduced pressure (such as a vacuum pump) to the cover in a manner so that an area of reduced pressure is created under the cover in the area of the wound. There are, however, certain instances where it is advantageous to have a wound treatment system that covers the entire portion of the body of the patient in the area of the wound, rather than merely the surface of the body immediately surrounding the wound. For example, certain types of burns that are treatable by reduced pressure may require treating a relatively large area of the patient's body with reduced pressure. In these cases, a device that covers the entire portion of the body to be treated would be advantageous.

In addition, it is possible to treat and alleviate certain other infirmities using reduced pressure. Such infirmities may include lymphedema, venous insufficiency and stasis, and varicose veins. In the case of lymphedema, the patient suffers from an abnormal interstitial accumulation of tissue fluid. The mechanism for this accumulation is impairment of normal fluid uptake by the lymphatic vessels or excessive production of tissue fluid, which is caused by venous obstruction that increases capillary blood pressure. Common causes of lymphedema include neoplastic obstruction of lymphatic flow, postoperative interference with lymphatic flow, infectious blockade of lymphatics, and radiation damage to lymphatics. In the case of venous insufficiency and stasis, blood circulation through the venous system is inadequate. This condition may be caused by congestion or by failure of the valves that regulate the flow of blood in the veins to operate normally. In the case of varicose veins, the veins become enlarged and dilated, which may lead to venous insufficiency and stasis. It is well known in the art that application of pressure to the portions of the body of the patient affected by these infirmities may provide relief from some of the symptoms of the infirmities. A device that is capable of enclosing and providing reduced pressure treatment to an entire portion of a patient's body affected by such infirmities would be advantageous because it would be capable of providing this required application of pressure.

Therefore, there is a need for a reduced pressure treatment system capable of enclosing the entire portion of a patient's body to be treated for a wound or other infirmity. There is also a need for such system to evenly distribute pressure on the surface of the portion of the body to be treated in certain instances. There is also a need for a reduced pressure treatment system to be flexible, so that it is adaptable to a wide variety of patient body shapes and contours. There is also a need for a reduced pressure treatment system that is simple to apply to the patient's body and simple to remove from the patient's body. In addition, there is a need for a reduced pressure treatment system that flexes with movement of the portion of the body being treated. Further, there is a need for a reduced pressure treatment system that provides for efficient removal of any fluid aspirated from the portion of the body being treated. There is also a need for a reduced pressure treatment system that provides a visual clue of loss of reduced pressure in the area of the wound under the enclosing means. Finally, there is also a need for a reduced pressure treatment system that is relatively inexpensive, while meeting the needs described above.

SUMMARY

The present invention is directed to a reduced pressure treatment appliance and methods that satisfy the needs described above. As described in greater detail below, they have many advantages over existing reduced pressure treatment apparatus and methods when used for their intended purpose, as well as novel features that result in a new reduced pressure treatment appliance and methods that are not anticipated, rendered obvious, suggested, or even implied by any of the prior art apparatus or methods, either alone or in any combination thereof.

In accordance with the present invention, a treatment appliance is provided for treating a portion of a body by applying reduced pressure (i.e., pressure that is below ambient atmospheric pressure) to the portion of the body to be treated in a controlled manner for a selected time period in a manner that overcomes the disadvantages of currently existing apparatus. For example, the application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached. In addition, applying reduced pressure to portions of the body affected by lymphedema, venous insufficiency and stasis, varicose veins, and other conditions provides benefits such as increasing the circulation of lymph through the lymphatic system, increasing the circulation of blood through the venous system, faster healing of such conditions, and relief from the symptoms of such conditions.

In a first aspect of the present invention, an appliance for treating a portion of a body is comprised of an enclosure having an opening, sealing means to seal the opening to the body, which are described in more detail below, and reduced pressure supply means, which are also described in more detail below. The enclosure is sized to be placed over and enclose the portion of the body to be treated. The enclosure and the sealing means allow reduced pressure to be maintained in the volume under the enclosure at the portion of the body to be treated. The reduced pressure supply means operably connect the enclosure to a reduced pressure supply source that provides a supply of reduced pressure to the enclosure, so that the volume under the enclosure at the portion of the body to be treated is supplied with reduced pressure by the reduced pressure supply source. In some embodiments of this first aspect of the invention, the enclosure has approximately the same shape as the portion of the body to be enclosed by the enclosure and is of a size adapted to enclose such portion of the body. In some of these embodiments, the enclosure may be comprised of a portion approximately in the shape of a human hand (including the fingers). In other embodiments, the enclosure may be comprised of a portion approximately in the shape of a human foot (including the toes). In still other embodiments, the enclosure may be comprised of a portion approximately in the shape of a mitten or a bootee. In yet other embodiments, the enclosure may be comprised of a flexible material, such as rubber, silicone, polyurethane, or any combination of such materials. In some of these embodiments, a portion of the enclosure may have a greater thickness than the remaining portion of the enclosure. The portion with the greater thickness may be positioned approximately adjacent to an area of the body requiring a reduced level of pressure. In other embodiments, the enclosure may be further comprised of at least one portion constructed of a rigid or semi-rigid material. In some of these embodiments, the at least one portion of the enclosure constructed of a rigid or semi-rigid material may be positioned approximately adjacent to an area of the body requiring a reduced level of pressure. Also, in some of these embodiments, the at least one portion may be constructed of metals, wood, ceramics, plastics and other polymers, such as polyvinyl chloride, or combinations of all such materials.

In some embodiments of this first aspect of the present invention, the enclosure is further comprised of at least one panel disposed thereon. In some of these embodiments, the at least one panel may be adapted to conform to the shape of at least a part of the portion of the body to be treated so that the at least one panel supports or immobilizes such part. In some of these embodiments, the at least one panel is comprised of a rigid or semi-rigid material or both. In some of these embodiments, the at least one panel may be comprised of metals, wood, ceramics, plastics and other polymers, or combinations of all such materials. In other embodiments of this first aspect of the present invention, the enclosure further comprises a port, so that the reduced pressure supply means is operably connected to the enclosure by means of the port. In some of these embodiments, the enclosure is further comprised of flow control means that are operably connected to the port. The flow control means permit fluids to flow from the volume under the enclosure at the portion of the body to be treated through the port to a volume outside the enclosure, but not in the opposite direction. In some of these embodiments, the flow control means may be a one-way valve. In some embodiments of this first aspect of the present invention, the port may be located approximately adjacent to the opening of the enclosure. In yet other embodiments, the port may be located approximately at the end of the enclosure that is distal from the opening of the enclosure. In other embodiments of this first aspect of the present invention, the enclosure is further comprised of channels disposed therein. In some of these embodiments, the channels may be operably connected to the port. The channels may generally provide for fluid aspirated from the portion of the body to be treated to flow along such channels to the port. In some embodiments, the channels are disposed on the surface of the enclosure facing the body. In yet other embodiments, at least one fold forms in the surface of the enclosure when reduced pressure is present under the enclosure at the portion of the body to be treated. In these embodiments, fluids aspirated by such portion of the body may flow along the at least one fold to the reduced pressure supply means, where they may be removed from the enclosure by means of the reduced pressure supply means cooperating with the reduced pressure supply source.

In some embodiments of this first aspect of the present invention, the area of the enclosure adjacent to the opening is comprised of a flexible material and the sealing means may be comprised of the suction of the area adjacent to the opening against the body, such suction being produced by the presence of reduced pressure in the volume under the enclosure at the portion of the body to be treated. In other embodiments, the sealing means may be comprised of an adhesive or adhesive tape that is disposed between the area of the enclosure adjacent to the opening and the portion of the body adjacent to such area of the enclosure. In yet other embodiments, the sealing means may be comprised of a material that is positioned approximately around the perimeter of the enclosure on the area of the enclosure adjacent to the opening. In still other embodiments, the appliance further comprises a suction drain extending from the reduced pressure supply means into the volume under the enclosure at the portion of the body to be treated. Suction drain connecting means, which are described in more detail below, are used to operably connect the reduced pressure supply means to the suction drain so that the suction drain is in fluid communication with the reduced pressure supply means and reduced pressure is supplied to the volume under the enclosure in the area of the wound by means of the suction drain.

In a second aspect of the present invention, the treatment appliance is comprised of a treatment device and a vacuum system. In various embodiments of this second aspect of the invention, the treatment device is comprised of an enclosure having an opening and sealing means to operably seal the opening to the body, wherein the enclosure and sealing means may generally have substantially the same structure, features, characteristics and operation as the appliance described above in connection with the first aspect of the invention. In this second aspect of the invention, the vacuum system is further comprised of a reduced pressure supply source that provides a supply of reduced pressure and reduced pressure supply means (which are described in more detail below) to operably connect the treatment device to the reduced pressure supply source, so that the volume under the treatment device at the portion of the body to be treated is supplied with reduced pressure by the reduced pressure supply source. In various embodiments of this second aspect of the invention, the reduced pressure supply means may generally have substantially the same structure, features, characteristics and operation as the reduced pressure supply means described above in connection with the first aspect of the invention.

In some embodiments of this second aspect of the invention, the reduced pressure supply source is comprised of a vacuum pump. In some of these embodiments, the reduced pressure supply source further comprises a control system for the vacuum pump, wherein the control system may control at least the level of suction produced by the vacuum pump or the rate of fluid flow produced by the vacuum pump, or any combination of rate of suction and rate of fluid flow of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms or fluids (or both) aspirated from the portion of the body to be treated. In yet other embodiments, the vacuum pump is comprised of a portable vacuum pump. In still other embodiments of this second aspect of the invention, the reduced pressure supply means is comprised of flexible tubing. In other embodiments, the reduced pressure supply means is further comprised of a collection system that is operably positioned between the treatment device and the reduced pressure supply source. In some of these embodiments, the collection system comprises a container to receive and hold fluid aspirated from the portion of the body to be treated and pressure halting means to halt the application of reduced pressure to the portion of the body to be treated when the fluid in the container exceeds a predetermined amount. In other embodiments of this second aspect of the invention, the reduced pressure under the enclosure at the portion of the body to be treated is in the range from approximately 20 mm of Hg below atmospheric pressure to approximately 125 mm of Hg below atmospheric pressure. In yet other embodiments, the reduced pressure is applied in a cyclic nature, the cyclic nature providing alternating time periods of application of reduced pressure and without application of reduced pressure.

In a third aspect of the invention, the treatment appliance is comprised of a treatment device and a vacuum system. In various embodiments of this third aspect of the invention, the treatment device is comprised of an enclosure and a seal. The enclosure is sized to be placed over and enclose the portion of the body to be treated and is adapted to maintain reduced pressure at the portion of the body to be treated. The seal operably seals the enclosure to the body at the portion of the body to be treated in a manner so that reduced pressure is maintained under the enclosure at the portion of the body to be treated. In addition, in the various embodiments of this third aspect of the invention, the vacuum system is comprised of a suction bulb, which may (but not necessarily) provide a source of reduced pressure, and reduced pressure supply means, which are described in more detail below, to operably connect the enclosure to the suction bulb, so that the portion of the body to be treated in the volume under the enclosure may be supplied with reduced pressure by the suction bulb. In some embodiments of this third aspect of the invention, the enclosure may be comprised of an enclosure that has substantially the same structure, features, characteristics and operation as the enclosure described above in connection with the first aspect of the invention. In some embodiments of this third aspect of the invention, the suction bulb is further comprised of an inlet port and an outlet port, wherein the inlet port is operably connected to the reduced pressure supply means, and the vacuum system further comprises an exhaust tubing member operably connected to the outlet port. In some of these embodiments, the vacuum system further comprises an exhaust control valve operably connected to the exhaust tubing member. In other embodiments, the vacuum system is further comprised of a filter operably connected to the exhaust tubing member, which prevents the venting of micro-organisms or fluids (or both) aspirated from the portion of the body to be treated. In yet other embodiments, the vacuum system is further comprised of a supplemental vacuum system that is operably connected to the exhaust tubing member. In these embodiments, the supplemental vacuum system may generally have substantially the same structure, features, characteristics and operation as the vacuum system described above in connection with the second aspect of the invention.

In other embodiments of the third aspect of the invention, the treatment device is further comprised of wound packing means, which are described in more detail below, that are positioned within a wound on the portion of the body to be treated. In these embodiments, the enclosure is placed over and encloses the wound and the wound packing means. In some embodiments, the wound packing means is comprised of absorbent dressings, antiseptic dressings, nonadherent dressings, water dressings, or combinations of such dressings. In other embodiments, the wound packing means is comprised of an absorbable matrix adapted to encourage growth of the tissue in the area of the wound under the enclosure into the matrix. The absorbable matrix is constructed of an absorbable material that is absorbed into the epithelial and subcutaneous tissue in the wound as the wound heals. In other embodiments of this third aspect of the invention, the treatment appliance further comprises a suction drain and suction drain connecting means, which are described in more detail below. The suction drain connecting means operably connect the reduced pressure supply means to the suction drain so that the suction drain is in fluid communication with the reduced pressure supply means and reduced pressure is supplied by means of the suction drain to the volume under the enclosure at the portion of the body to be treated. In these embodiments, the suction drain extends from the reduced pressure supply means into the volume under the enclosure in the area of the wound. In some of these embodiments, the suction drain is further comprised of a distal end portion and the distal end portion has at least one perforation in the surface thereof. In some of these embodiments, the distal end portion of the suction drain is positioned within the interior volume of the wound packing means.

A fourth aspect of the present invention discloses a method of treating a portion of a body. In one embodiment of this fourth aspect of the invention, the method comprises the following steps. First, an enclosure is positioned on the body over the portion of the body to be treated, wherein the enclosure has an opening and is sized to be placed over and enclose the portion of the body to be treated. The enclosure is also adapted to maintain reduced pressure at the portion of the body to be treated. Second, the area of the enclosure adjacent to the opening is operably sealed to the body so that reduced pressure may be maintained in the volume under the enclosure at the portion of the body to be treated. Third, the enclosure is operably connected with a vacuum system for producing reduced pressure in the volume under the enclosure at the portion of the body to be treated. Fourth, the reduced pressure is maintained until the portion of the body to be treated has progressed toward a selected stage of healing. In other embodiments of this fourth aspect of the invention, the vacuum system is comprised of a suction bulb and the method further comprises the step of squeezing the suction bulb to reduce its volume and then releasing the suction bulb, so that reduced pressure is produced in the volume under the enclosure at the portion of the body to be treated. In other embodiments of this fourth aspect of the first version of the invention, the reduced pressure under the enclosure at the portion of the body to be treated is in the range from approximately 20 mm of Hg below atmospheric pressure to approximately 125 mm of Hg below atmospheric pressure. In still other embodiments of this fourth aspect of the first version of the invention, the reduced pressure is applied in a cyclic nature, the cyclic nature providing alternating time periods of application of reduced pressure and without application of reduced pressure. In other embodiments, the method further comprises the step of placing wound packing means between the portion of the body to be treated and the enclosure, such step being performed prior to positioning the enclosure over the portion of the body to be treated. In still other embodiments, the method further comprises the step of placing a liner over the portion of the body to be treated, wherein the liner is disposed between the portion of the body to be treated and the enclosure, such step being performed prior to positioning the enclosure over the portion of the body to be treated. It is to be noted that in various other embodiments, the steps described above may be performed in a different order than that presented.

As is illustrated in the detailed descriptions herein, the treatment appliance of the present invention meets the needs discussed above in the Background section. For example, the treatment appliance and methods disclosed herein are capable of enclosing and applying reduced pressure to the entire portion of a patient's body to be treated for a wound or other infirmity. In certain embodiments, the treatment appliance may also evenly distribute pressure on the surface of the portion of the body to be treated. In other embodiments, the treatment appliance has the flexibility to provide differing levels of pressure on the surface of the patient's body. The disclosed treatment appliance is also flexible, so that it is adaptable to a wide variety of patient body shapes and contours. The disclosed treatment appliance is also simple to apply to the patients body and simple to remove from the patient's body. In addition, the treatment appliance has the capability to flex with the movement of the portion of the body being treated. Further, the treatment appliance provides for efficient removal of any fluid aspirated from the portion of the body being treated by means of folds that form in the surface as the enclosure collapses or by means of channels comprising the enclosure. In addition, the enclosure of the treatment appliance provides a visual clue of loss of reduced pressure in the area of the wound under the enclosure. For example, if reduced pressure is lost under the enclosure, the enclosure will expand outward from the portion of the body it encloses, providing a visual indication that reduced pressure has been lost. Because it is simple in construction and may be constructed from readily available materials, the treatment appliance should also be relatively inexpensive, while meeting the needs described above. Finally, it is to be noted that the treatment appliance disclosed herein is not limited to treatment of the types of wounds, conditions, and infirmities disclosed herein, but may instead be used in the treatment and diagnosis of any wound, condition or infirmity for which application of reduced pressure is suitable or desirable.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION OF THE PREFERRED EMBODIMENT

In accordance with the present invention, a treatment appliance is provided for treating all or a portion of the body of a patient by applying reduced pressure (i.e., pressure that is below ambient atmospheric pressure) to the portion of the body to be treated in a controlled manner for a selected time period in a manner that overcomes the disadvantages of currently existing apparatus. One embodiment of a first aspect of the invention is the treatment appliance 10 illustrated in FIG. 1A and FIG. 1B. In this embodiment, the treatment appliance is comprised of an enclosure 20 having an opening 21 at one end, sealing means to seal the opening 21 to the body (not illustrated), which are described in more detail below, and reduced pressure supply means, which are also described in more detail below. The enclosure 20 is generally sized to be placed over and enclose the portion of the body to be treated. The enclosure 20 and the sealing means (described in more detail below) allow reduced pressure to be maintained in the volume under the enclosure 20 at the portion of the body to be treated, as described in more detail below. The reduced pressure supply means (not illustrated) are used to operably connect the enclosure 20 to a reduced pressure supply source (also not illustrated) in a manner so that the reduced pressure supply source provides a supply of reduced pressure to the enclosure 20, so that the volume under the enclosure 20 at the portion of the body to be treated may be maintained at reduced pressure.

Figure 1A:
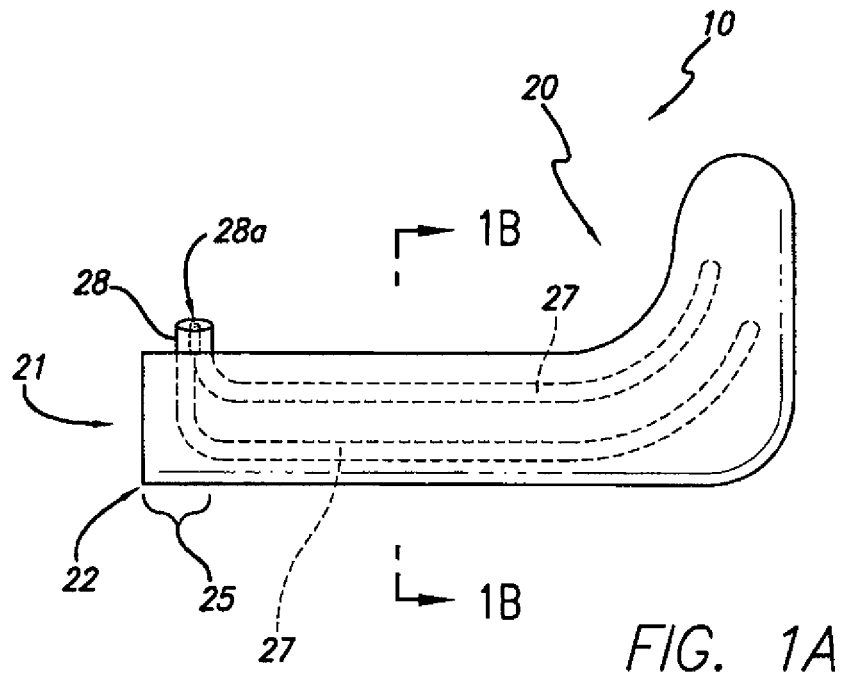
FIG. 1A is a plan view of an embodiment of an enclosure comprising the present invention.
Figure 1B:
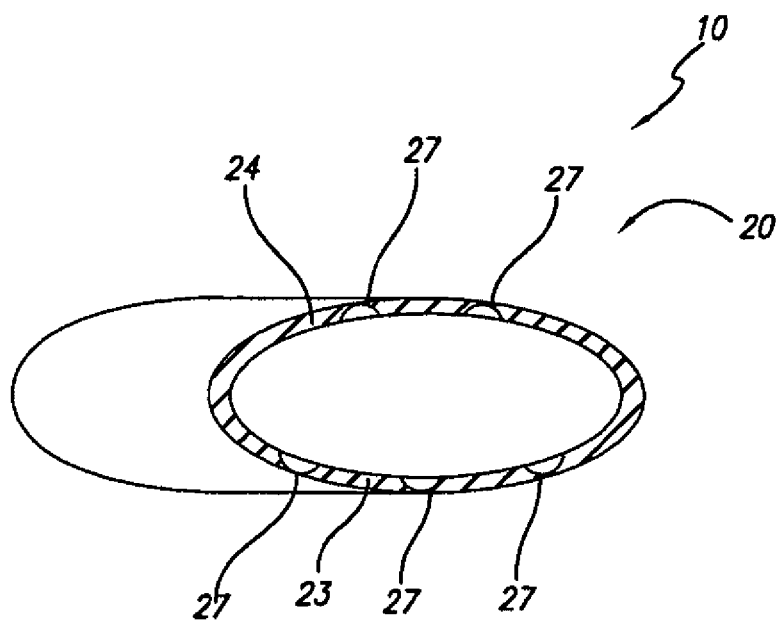
FIG. 1B is a cross-sectional elevation view of the embodiment of the enclosure illustrated in FIG. 1A, as taken along the lines 1B-1B of FIG. 1A, illustrating a pattern of channels comprising the enclosure.
Figure 3A:
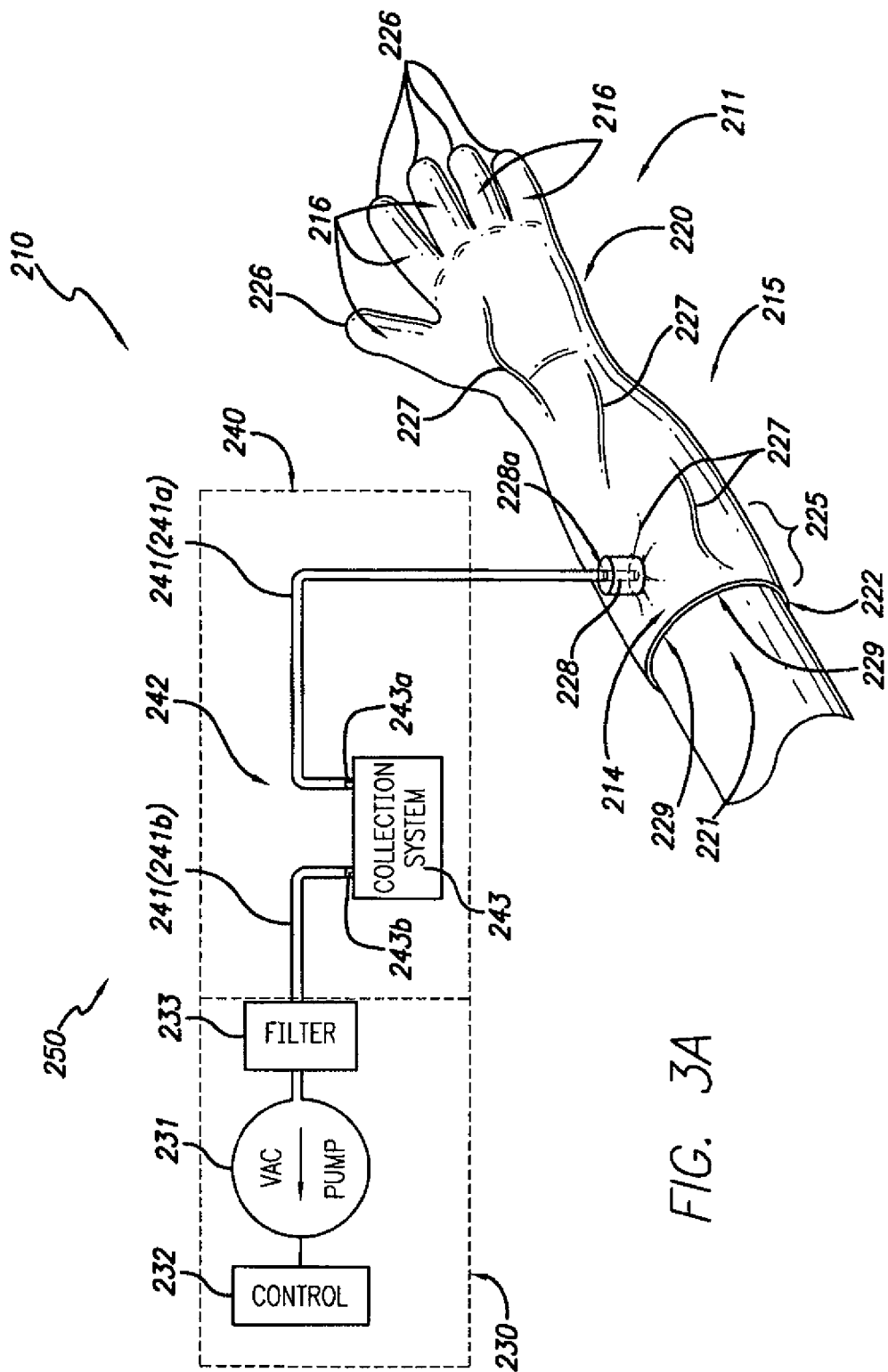
FIG. 3A is a view of an embodiment of a treatment appliance comprising the present invention, in which an embodiment of a treatment device, shown in perspective view, encloses the lower arm portion of a patient, and in which an embodiment of a vacuum system, depicted generally and shown in schematic elevation view, provides reduced pressure within the volume under the enclosure comprising the treatment device.
Figure 4:
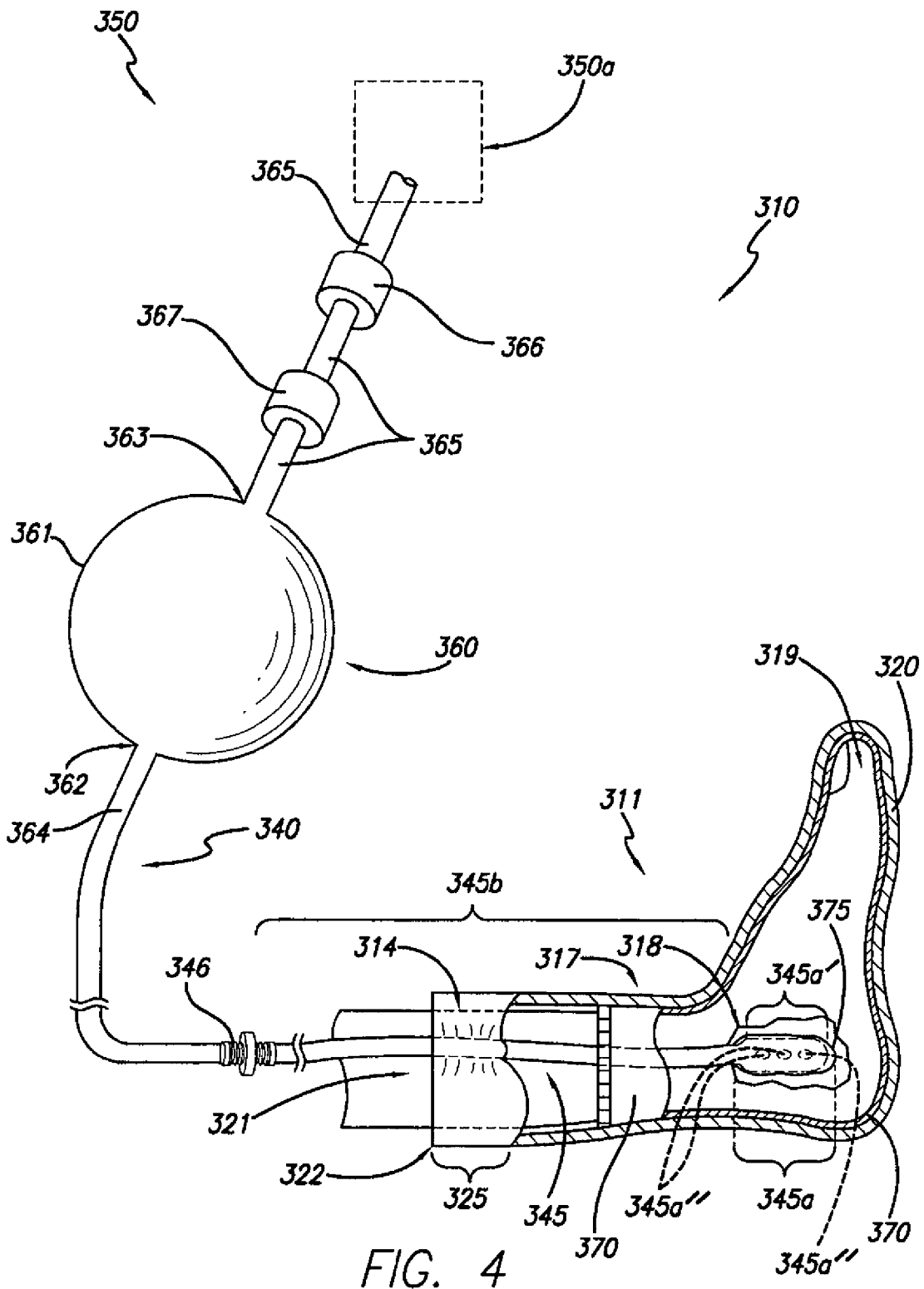
FIG. 4 is a view of an embodiment of a treatment appliance comprising the present invention, in which an embodiment of a treatment device, shown in elevational partial cross sectional view, encloses the lower leg portion of a patient, and in which an embodiment of a vacuum system, shown in elevational view, provides reduced pressure within the volume under the enclosure comprising the treatment device.

In the illustrated embodiment, the enclosure 20 is of the shape illustrated in FIG. 1A and FIG. 1B, having an opening 21 at one end of the illustrated shape with an opening perimeter 22 adjacent to the opening 21. The enclosure 20 illustrated in FIG. 1 is in its natural shape, as it exists prior to being applied to a patient for treatment of a portion of the body of the patient. In this embodiment, as illustrated in FIG. 1B, the enclosure 20 is generally comprised of a flexible material, so that it tends to lie flat when not in use. Thus, in the view of the enclosure 20 illustrated in FIG. 1B, the enclosure 20 appears partially folded, having a lower portion 23 and an upper portion 24. This embodiment of the enclosure 20 may be used to treat a number of body portions. For example, the enclosure 20 may be used to enclose and provide treatment to extremital body portions, such as feet, ankles, hands, and wrists. Larger enclosures 20 may be used to enclose and provide treatment to larger extremities, such as portions of the leg below the hip and portions of the arm below the shoulder. Smaller enclosures 20 may be used to enclose and provide treatment to smaller extremities, such as toes and fingers. Other embodiments of the enclosure 20 may be used to enclose and treat multiple extremities, such as more than one finger. In still other embodiments, the enclosure 20 may be used to enclose a portion of the torso, head or other portion of the patients body. In operation, the opening 21 of the enclosure 20 is placed over the portion of the body for which treatment is desired and the enclosure 20 is pulled over the body until the desired body portion is covered by the enclosure 20. The shape of the enclosure 20 of FIG. 1A and FIG. 1B is particularly suited to treatment of portions of the leg below the knee. In other embodiments, the enclosure 20 may have almost any shape and be of almost any size desired to fit the portion of the body to be treated. For example, in the embodiment of this first aspect of the invention illustrated in FIG. 2, the enclosure 120 is generally shaped as a mitten. Although this embodiment of the enclosure 120 may be used to treat other body portions, it is particularly suited to treatment of hands, wrists and portions of the arm below the elbow or shoulder. In other embodiments of this first aspect of the invention, as illustrated in FIG. 3A, the enclosure 220 may have approximately the same shape and size as the portion of the body (the lower arm 215 in this embodiment) to be enclosed and treated by the enclosure 220. In the illustrated embodiment, the enclosure 220 is approximately in the shape of a human hand (including the fingers) and wrist and is sized to fit over and enclose the hand (including the fingers) and wrist. As another example, in other embodiments the enclosure may be approximately in the shape of a human foot, including the toes. In still other embodiments, as illustrated in FIG. 4, the enclosure 320 may be approximately in the shape of a bootee. Referring again to the embodiment illustrated in FIG. 1A and FIG. 1B, the preferred shape and size of the enclosure 20 is generally dependent upon the shape and size of the portion of the body to be treated, the type of wound or condition to be treated, the level of reduced pressure to be used in the treatment, the duration for which the enclosure 20 will be used for treatment purposes, the individual preference of the user of the appliance 10, and other factors related to the sealing means, reduced pressure supply means, and use of a suction drain (if any), as described in more detail below.

In the various embodiments of this first aspect of the invention, the enclosure 20, 120, 220, 320 may be comprised of almost any flexible medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of conforming to the contours of the surface of the portion of the body enclosed by the enclosure, as described in more detail below. For example, the enclosure 20, 120,220,320 may be comprised of rubber (including neoprene) or flexible polymer materials, such as silicone, silicone blends, polyurethane or similar polymers, or combinations of all such materials. Preferably, the enclosure 20, 120, 220, 320 is comprised of silicone or a silicone blend. It is to be noted that in various embodiments of this first aspect of the invention, the enclosure 20, 120, 220, 320 may be constructed in whole or in part of gas-permeable materials, allowing limited amounts of oxygen to penetrate the enclosure 20, 120, 220, 320 so that the portion of the body under the enclosure 20,120,220,320 can "breathe." In some embodiments, all portions of the enclosure 20,120, 220, 320 are preferably constructed of one type of flexible material, such as silicone. In some of these embodiments, the thickness of various portions of the enclosure 20,120,220,320 may vary in order to vary the level of pressure exerted by the enclosure 20, 120, 220, 320 at the portion of the body adjacent to the portions. For example, in embodiments of the enclosure 220 illustrated in FIG. 3A, the thumb and finger portions 226 of the enclosure 220 may have a greater thickness than the remaining portion of the enclosure 220. In these embodiments, the thumb and finger portions 226 of the enclosure 220 will not collapse against the fingers 216 with the same force as the remaining portions of the enclosure 220 collapse against the body when suction is produced by the application of reduced pressure in the volume under the enclosure 220. The reason is the increased stiffness of the thumb and finger portions 226 caused by the increased thickness of such portions 226. In yet other embodiments of this first aspect of the invention, as illustrated in FIG. 3A, the enclosure 220 is of a thickness so that at least one fold 227 forms in the surface of the enclosure 220 when reduced pressure is present under the enclosure 220 at the portion 215,216 of the body to be treated. In these embodiments, fluids aspirated by such portion 215, 216 of the body may flow along the at least one fold 227 to the reduced pressure supply means 240, where they may be removed from the enclosure 220 by means of the reduced pressure supply means 240 cooperating with the reduced pressure supply source 230, as described in more detail below. It is also to be noted that in various embodiments of the first aspect of the invention, different portions of the enclosure 20, 120, 220, 320 may be constructed of different materials. For example, in the embodiment of the enclosure 20 illustrated in FIG. 1A and FIG. 1B, the portion 25 of the enclosure 20 adjacent to the opening 21 may be constructed of a more flexible material than the remaining portions of the enclosure 20 to provide for a more effective sealing means, as described in more detail below. In other embodiments, and referring again to FIG. 3A, the enclosure 220 may also be comprised of at least one portion constructed of a rigid or semi-rigid material. Generally, in these embodiments, the at least one portion of the enclosure 220 constructed of a rigid or semi-rigid material may be positioned approximately adjacent to an area of the body requiring a reduced level of pressure or support. For example, the thumb and finger portions 226 of the enclosure 220 may be constructed of a semi-rigid material in order to keep such portions 226 from collapsing against the fingers when reduced pressure is applied to the volume under the enclosure 220. In addition, the thumb and finger portions 226 may be constructed of a rigid material in order to provide support for the fingers 216, so that they are held in a designated position during the treatment using the enclosure 220. As another example, a portion of the enclosure 220 adjacent to the wrist portion 215 of the patient may be constructed of a rigid or semi-rigid material to immobilize or provide support for the wrist portion 215. In some of the embodiments comprising at least one rigid or semi-rigid portion, such portion may be constructed of metals, wood, ceramics, plastics and other polymers, such as polyvinyl chloride, or combinations of all such materials. Generally, the enclosure 20, 120, 220, 320 may be constructed using any suitable means currently known in the art or that may be developed in the art in the future. For example, an enclosure 20, 120, 220, 320 constructed entirely of silicone may be manufactured by means of injection molding. As another example, embodiments of enclosures 20, 120, 220, 320 constructed of different types of materials may be constructed by fusing or welding such portions together. Referring again to FIG. 1A as an example, it is also to be noted that in various embodiments of this first aspect of the invention, a portion of the enclosure 20 adjacent to the opening 21 may be cut away from the enclosure 20 in order to adapt the enclosure 20 for use with a smaller sized portion of the body to be treated.

The preferred thickness of the enclosure 20, 120, 220, 320 is dependent upon the size and shape of the enclosure 20, 120, 220, 320, the size, shape and contour of the portion of the body to be covered by the enclosure 20, 120, 220, 320, the magnitude of the reduced pressure to be maintained under the enclosure 20, 120, 220, 320, the materials comprising the enclosure 20, 120, 220, 320, and the individual preferences of the user of the enclosure 20, 120, 220, 320. For example, in the embodiment illustrated in FIG. 1A, for an enclosure 20 constructed entirely of silicone, having the illustrated shape, being of a uniform thickness, and being sized to treat the lower leg portion of an adult human, the preferred thickness of the enclosure 20 is in the range from 1/32" inches to 1½" inches. More preferred in this embodiment, the thickness of the enclosure 20 is approximately 3/8" inches. It is to be noted that in other embodiments the thickness of the enclosure 20, including any rigid or semi-rigid portions of the enclosure 20, may vary from embodiment to embodiment, as well as from location to location on the enclosure 20.

Figure 2:
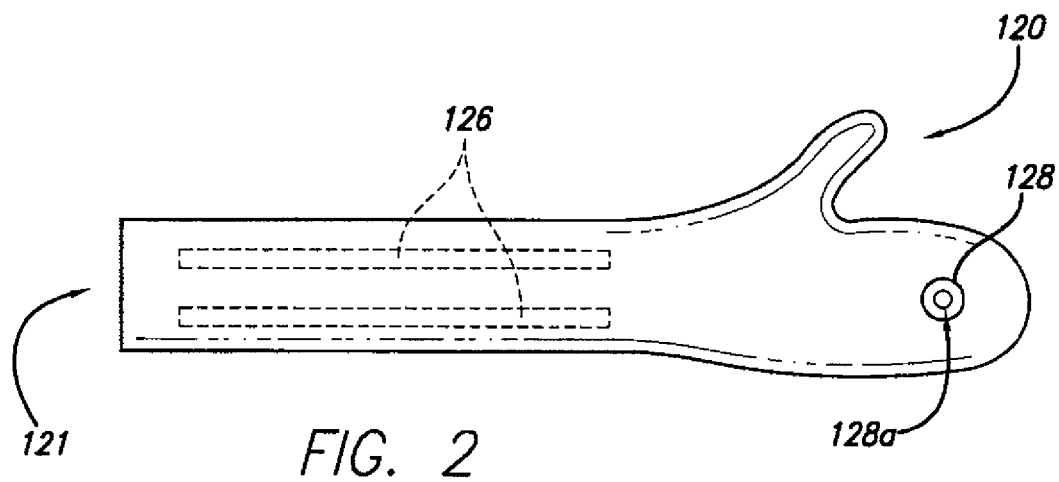
FIG. 2 is a plan view of another embodiment of an enclosure comprising the present invention.

In some embodiments of this first aspect of the present invention, as illustrated in FIG. 2, the enclosure 120 may be further comprised of at least one panel 126 disposed thereon. For example, in the illustrated embodiment, the panels 126 are comprised of a rigid or semi-rigid material and may be permanently or removably attached to the surface of the enclosure 120. The panels 126 may be used to provide support for or to immobilize a portion of the body (the wrist, in the case of use of the enclosure 120 to treat the portion of the arm below the elbow) during the treatment process. In the case of permanent attachment, the panels 126 may be attached to the enclosure 120 by means of adhesives, glues, welding, fusing, rivets, or other fasteners or combination of all such means. In the case of removable attachment, the panels 126 may be attached to the enclosure 120 by means of hook and loop fasteners (such as VELCRO), zippers, or other detachable connectors or combinations of all such means. In other embodiments, the panels 126 may be slid into a pockets or sheaths that are located on a surface of the enclosure 120. In various embodiments, one or more of the panels 126 may be adapted to conform to the shape of at least a part of the portion of the body to be treated so that the panels 126 support or immobilize such part in a manner comfortable to the patient. In various embodiments, the panels 126 may be comprised of a rigid or semi-rigid material or both. In some of these embodiments, the at least one panel may be comprised of metals, wood, ceramics, plastics and other polymers, or combinations of all such materials.

Figure 1C:
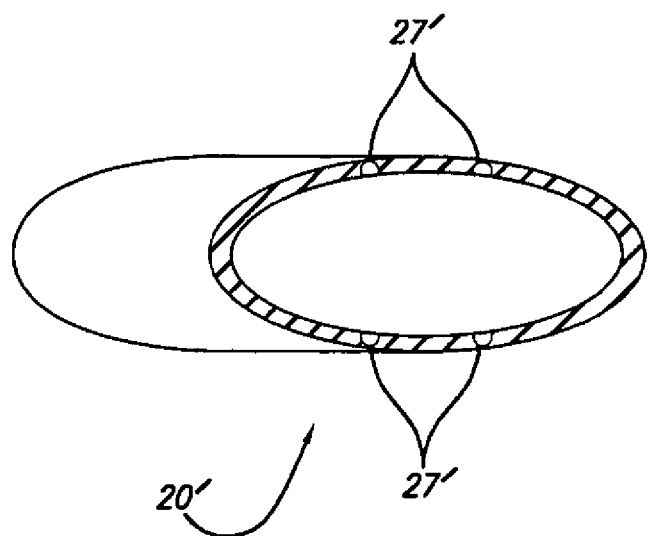
FIG. 1C is a cross-sectional elevation view of an embodiment of the enclosure illustrated in FIG. 1A, as taken along the lines 1B-1B of FIG. 1A, illustrating another embodiment of a pattern of channels comprising the enclosure.

In other embodiments of this first aspect of the present invention, as illustrated in FIG. 1A and FIG. 1B, the enclosure 20 may be further comprised of channels 27 disposed therein. The channels 27 may generally provide for fluid aspirated from the portion of the body to be treated to flow along such channels 27 to the reduced pressure supply means (not illustrated), where the fluids may be removed from the enclosure 20 by means of the reduced pressure supply means cooperating with the reduced pressure supply source, as described in more detail below. In some of these embodiments, the channels 27 may be operably connected to the reduced pressure supply means through a port 28. In the illustrated embodiment, there are two continuous channels 27 recessed into the interior surface of the upper portion 24 of the enclosure 20 and three continuous channels 27 recessed into the interior surface of the lower portion 23 of the enclosure 20. In other embodiments, the channels 27 may be disposed in other positions relative to the enclosure 20. For example, as illustrated in FIG. 1C, the channels 27' may be in the form of tubes 27' positioned within the volume of the enclosure 20', wherein the tubes 27' have one or more perforations so that the channels 27' are in fluid communication with the volume under the enclosure 20 in the area of the body to be treated. In other embodiments, the channels 27' may be in the form of tubes that extend along the interior surface (the surface facing the portion of the body to be treated) of the enclosure 20' rather than the volume within the enclosure 20', wherein the tubes have one or more openings so that the tubes 27' are in fluid communication with the volume under the enclosure 20' in the area of the body to be treated. The channels 27, 27' may be of almost any size and shape to accomplish their intended purpose. The preferred size and shape is dependent upon the size and shape of the enclosure 20, the type of wound or condition to be treated, the level of reduced pressure to be used in the treatment, the amount of fluid anticipated, the type of reduced pressure supply means utilized, and the individual preference of the user of the appliance 10. Where utilized, channels 27, 27' may be molded or cut into the surface of the enclosure 20 or, if in the shape of exterior tubes, may be molded as a part of the surface of the enclosure 20 or may be welded or fused to the surface of the enclosure 20.

In some embodiments of this first aspect of the present invention, as illustrated in FIG. 1A, the enclosure 20 further comprises a port 28. The port 28 is adapted to be of a size and shape so that the reduced pressure supply means may be operably connected to the enclosure 20 by means of the port 28. When the port 28 is operably connected to the reduced pressure supply means, reduced pressure may be supplied to the volume under the enclosure 20 at the portion of the body to be treated. Although the port 28 is positioned at a location approximately adjacent to the opening 21 of the enclosure 20 in the embodiment illustrated in FIG. 1A, the port 28 may be located at other locations on the enclosure 20 in other embodiments. For example, in the embodiment of the enclosure 120 illustrated in FIG. 2, the port 128 is located on a surface of the enclosure 120 near the end of the enclosure 120 distal from the opening 121 of the enclosure 120. Referring again to FIG. 1A as an example, in various embodiments, the port 28 may be located at almost any location on the surface of the enclosure 20 as long as the port 28 does not adversely affect the ability of the opening 21 of the enclosure 20 to make an operable seal with the surface of the body adjacent to the opening 21, as described in more detail below. For example, the port 28 may not be located too close to the perimeter 22 of the opening 21 of the enclosure 20 because an operable seal with the surface of the body is typically formed at that location. Although the port 28 may be constructed of a material different from the material comprising the remainder of the enclosure 20 in various embodiments of the invention, the port 28 is preferably constructed from the same material comprising the remainder of the enclosure 20. In the embodiments of the enclosure 20, 120 illustrated in FIG. 1A and FIG. 2, respectively, the ports 28,128 are generally cylindrical in shape and are further comprised of an approximately cylindrical channel 28a, 128a, respectively, that extends from the top of each of the ports 28,128, respectively, to the bottom of the ports 28,128, respectively. The ports 28, 128 of these embodiments are thus able to receive a vacuum system or reduced pressure supply means, which are described in more detail below, adapted to be connected to this shape of port 28, 128, respectively, and channel 28a, 128a, respectively. In other embodiments of this first aspect of the invention, the ports 28, 128 or the channels 28a, 128a, respectively, or both may have different shapes and configurations as may be desired to adapt and connect the ports 28, 128, respectively, and the channels 28a, 128a, respectively, to the vacuum system or reduced pressure supply means, which are described in more detail below. In some of the embodiments comprising a port 28, 128, the enclosure 20, 120 is further comprised of flow control means that are operably connected to the port 28, 128. The flow control means permit fluids to flow from the volume under the enclosure 20, 120 at the portion of the body to be treated through the port 28, 128 to a volume (such as the reduced pressure supply means) outside the enclosure 20,120, but not in the opposite direction. In some of these embodiments, the flow control means may be a one-way valve that is located within the channel 28a, 128a in the port 28, 128. Such valves are well known in the relevant art. In other embodiments of this first aspect of the invention, a means of connecting the enclosure 20, 120 to the reduced pressure supply means (described in more detail below) may be located on the enclosure 20, 120 in lieu of or in conjunction with the port 28,128. For example, in some embodiments, the port 28, 128 may be combined with a variable descending diameter adapter (commonly referred to as a "Christmas tree" adapter).

An embodiment of a second aspect of the present invention is the treatment appliance 210 illustrated in FIG. 3A. In this embodiment, the treatment appliance 210 is comprised of a treatment device 211 and a vacuum system, generally designated 250, that is operably connected to, and provides a supply of reduced pressure to, the treatment device 211. Also in this embodiment, the treatment device 211 is comprised of an enclosure 220. In addition, in this embodiment, the vacuum system 250 is further comprised of a reduced pressure supply source, generally designated 230, which is illustrated schematically and described in more detail below, and reduced pressure supply means, generally designated 240, which are illustrated schematically and described in more detail below. Also in this embodiment, the reduced pressure supply means 240 are used to connect the reduced pressure supply source 230 to the enclosure 220 in a manner so that reduced pressure is supplied to the volume under the enclosure 220 at the portion of the body 215, 216 to be treated, as described in more detail below. In the embodiment of the second aspect of the invention illustrated in FIG. 3A, the enclosure 220 has substantially the same structure, features, characteristics and operation as described above and illustrated in connection with the first aspect of the invention. It is to be noted, however, that in other embodiments of this second aspect of the invention, the enclosure 220 may have substantially the same structure, features and characteristics as any embodiment of all of the enclosures 20,120,220,320 of the first aspect of the invention described above and illustrated in connection with FIG. 1A, FIG. 1B, FIG. 1C, FIG. 2, FIG. 3, and FIG. 4.

In the various embodiments of this second aspect of the present invention, as illustrated in FIG. 3A, the portion 225 of the enclosure 220 adjacent to the opening 221 of the enclosure 220 is comprised of a flexible material and the sealing means is comprised of the suction of the portion 225 adjacent to the opening 221 against the portion 214 of the body adjacent to such portion 225 of the enclosure 220, such suction being produced by the presence of reduced pressure in the volume under the enclosure 220 at the portion 215, 216 of the body to be treated. In other embodiments, the sealing means may be comprised of an adhesive, an adhesive tape, lanoline, or other sealant, or any combination of such means, that is disposed between the portion 225 of the enclosure 220 adjacent to the opening 221 and the portion 214 of the body adjacent to such portion 225 of the enclosure 220. In yet other embodiments, the sealing means may be comprised of a material (not illustrated) that is positioned approximately around the perimeter of the enclosure 220 on the portion 225 of the enclosure 220 adjacent to the opening 221. This material is used to hold such portion 225 against the adjacent portion 214 of the body. For example, an elastic bandage or adhesive tape may be wrapped around the portion 225 of the enclosure 220 adjacent to the opening 221. The material may also overlap the perimeter 222 of the enclosure 220 and be placed against the body.

In the embodiment illustrated in FIG. 3A, the reduced pressure supply source 230 of the vacuum system 250, which produces a source of reduced pressure or suction that is supplied to the enclosure 220, is comprised of a vacuum pump 231, a control device 232, and a filter 233. Although the preferred means of producing the reduced pressure or suction is a vacuum pump 231 in this embodiment, in other embodiments of this second aspect of the invention other means may be used, such as an outlet port of a centralized hospital vacuum system. In the illustrated embodiment, predetermined amounts of suction or reduced pressure are produced by the vacuum pump 231. The vacuum pump 231 is preferably controlled by a control device 232, such as a switch or a timer that may be set to provide cyclic on/off operation of the vacuum pump 231 according to user-selected intervals. Alternatively, the vacuum pump 231 may be operated continuously without the use of a cyclical timer. In addition, in some embodiments the control device 232 may provide for separate control of the level of reduced pressure applied to the volume under the enclosure 220 at the portion 215, 216 of the body to be treated and the flow rate of fluid aspirated from such portion 215, 216 of the body, if any. In these embodiments, relatively low levels of reduced pressure may be maintained at the portion 215, 216 of the body to be treated under the treatment device 211, while still providing for the removal of a relatively large volume of exudate from the portion 215, 216 of the body to be treated. A filter 233, such as a micropore filter, is preferably attached to the inlet of the vacuum pump 231 to prevent potentially pathogenic microbes or aerosols from contaminating, and then being vented to atmosphere by, the vacuum pump 231. In other embodiments, the filter 233 may also be a hydrophobic filter that prevents any exudate from the wound from contaminating, and then being vented to atmosphere by, the vacuum pump 231. It is to be noted that in other embodiments of the invention, the reduced pressure supply source 230 may not have a filter 233 or a control 232 or any combination of the same.

In other embodiments of the second aspect of the invention, the reduced pressure supply source 230 of the vacuum system 250, may be comprised of a small, portable vacuum pump 231. In some of these embodiments, a filter 233 or a power source (not illustrated), or both, may also be contained within the housing for the portable vacuum pump 231. In these embodiments, the portable vacuum pump 231 is preferably controlled by a control device 232 that is also located within the housing for the portable vacuum pump 231, which may provide substantially the same functions as the control device 232 described above. Except for its smaller size, the portable vacuum pump 231 may operate in substantially the same manner as the vacuum pump 231 described above. Also, in these embodiments, the filter 233 may have the same structure, features, characteristics and operation, and provide substantially the same functions, as the filter 233 described above. In some of these embodiments, the filter 233 may be rigidly connected to the portable vacuum pump 231. The power source may be any source of energy currently known in the art or that may be developed in the art in the future that may be used to power the portable vacuum pump 231. For example, in some embodiments, the power source may be a fuel cell or battery.

In the embodiment of the second aspect of the invention illustrated in FIG. 3A, the reduced pressure supply means 240 of the vacuum system 250, which are used to connect the reduced pressure supply source 230 to the enclosure 220 so that reduced pressure is supplied to the volume under the enclosure 220 at the portion 215, 216 of the body to be treated is comprised of at least one tubing member 241. In this embodiment, the at least one tubing member 241 is sufficiently flexible to permit movement of the at least one tubing member 241, but is sufficiently rigid to resist constriction when reduced pressure is supplied to the enclosure 220 or when the location of the portion 215,216 of the body to be treated is such that the patient must sit or lie upon the at least one tubing member 241 or upon the treatment device 211. In the embodiment illustrated in FIG. 3A, the at least one tubing member 241 is connected to the enclosure 220 by inserting one end of the at least one tubing member 241 into an opening 228a of a port 228 of the enclosure 220. In this embodiment, the at least one tubing member 241 is held in place in the opening 228a by means of an adhesive. It is to be noted that in other embodiments of this second aspect of the invention, the at least one tubing member 241 may be connected to the port 228 of the enclosure 220 using any suitable means currently known in the art or developed in the art in the future. Examples include variable descending diameter adapters (commonly referred to as "Christmas tree" adapters), luer lock fittings and adapters, clamps, and combinations of such means. Alternatively, the port 228 and the at least one tubing member 241 may be fabricated as a single piece. Similar means may be used to connect the other end of the at least one tubing member 241 to the vacuum pump 231 or other reduced pressure supply source 230 providing the reduced pressure.

Figure 3B:
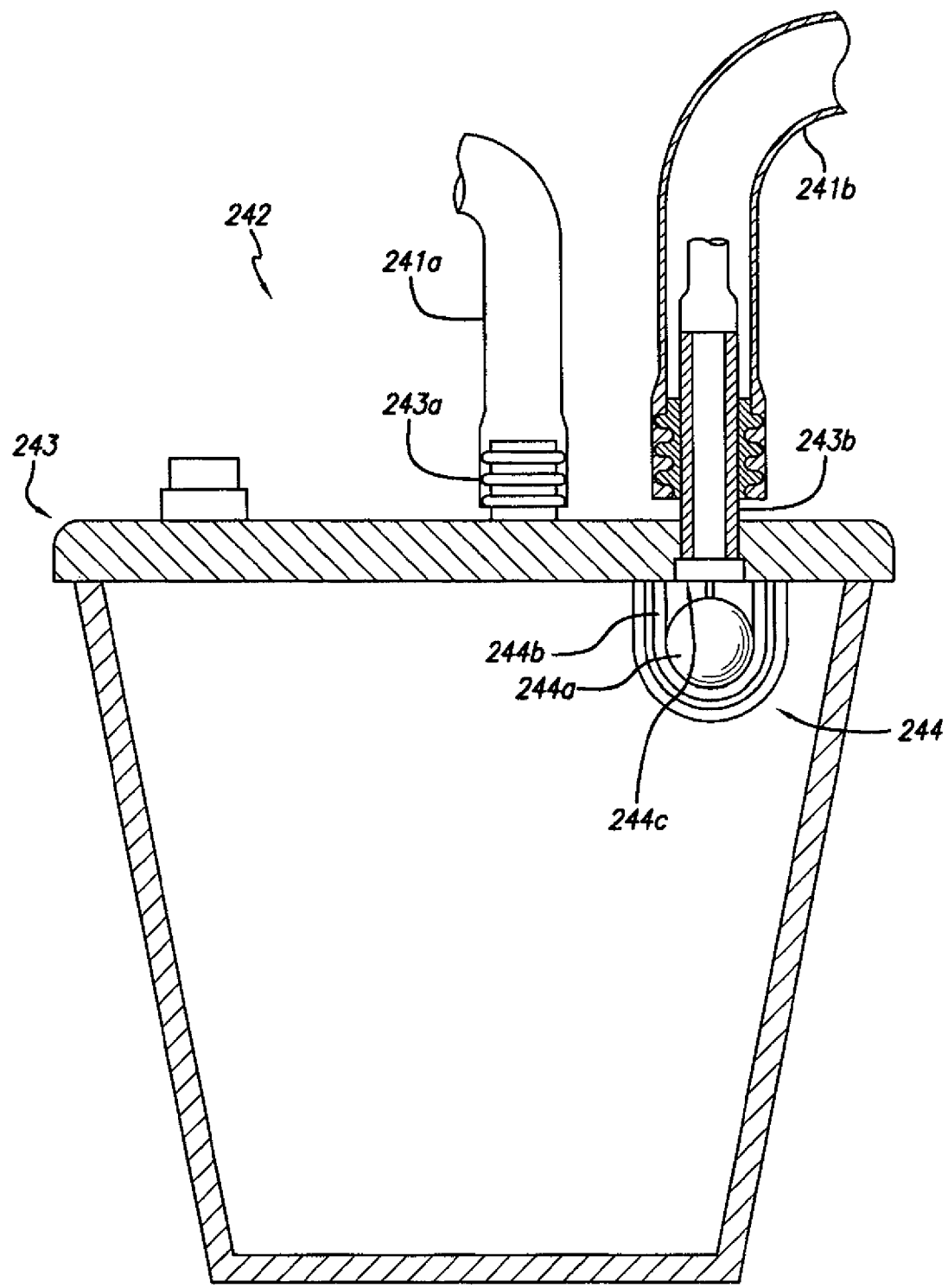
FIG. 3B is a sectional elevational detailed view of an embodiment of a collection container and the shutoff mechanism portion of the collection system of FIG. 3A.

In the embodiment illustrated in FIG. 3A, the reduced pressure supply means 240 further comprise a fluid collection system, generally designated 242, that is interconnected between the suction pump 231 and the enclosure 220 to remove and collect any exudate that may be aspirated from the portion 215, 216 of the body to be treated and collected by the enclosure 220. The enclosure 220 functions to actively draw fluid or exudate from the portion 215, 216 of the body to be treated. Collection of exudate in a fluid collection system 242 intermediate the pump 231 and the enclosure 220 is desirable to prevent clogging of the pump 231. The fluid collection system 242 is comprised of a fluid-impermeable collection container 243 and a shutoff mechanism 244, which are described in more detail below in connection with FIG. 3D. The container 243 may be of any size and shape capable of intercepting and retaining a predetermined amount of exudate. Many examples of such containers are available in the relevant art. Referring to FIG. 3B, which is an enlarged elevational cross-sectional view of the preferred embodiment of the container 243, the container 243 includes a first port 243a at the top opening of the container 243 for sealed connection to tubing member 241a, where the other end of the tubing member 241a is connected to the enclosure 220. The first port 243a enables suction to be applied to the enclosure 220 through the tubing 241a and also enables exudate from the portion 215, 216 of the body enclosed by the enclosure 220 to be drained into the container 243. The container 243 provides a means for containing and temporarily storing the collected exudate. A second port 243b is also provided on the top of the container 243 to enable the application of suction from the vacuum pump 231. The second port 243b of the collection system 242 is connected to the vacuum pump 231 by tubing member 241b. The collection system 242 is sealed generally gas-tight to enable the suction pump 231 to supply suction to the enclosure 220 through the collection system 242.

The embodiment of the collection system 242 illustrated in FIG. 3B also includes a shutoff mechanism for halting or inhibiting the supply of reduced pressure to the enclosure 220 in the event that the exudate aspirated from the portion 215, 216 of the body to be treated exceeds a predetermined quantity. Interrupting the application of suction to the enclosure 220 is desirable to prevent exsanguination in the unlikely event a blood vessel ruptures under the enclosure 220 during treatment. If, for example, a blood vessel ruptures in the vicinity of the enclosure 220, a shut-off mechanism would be useful to prevent the vacuum system 250 from aspirating any significant quantity of blood from the patient. In the preferred embodiment of the shutoff mechanism 244, as illustrated in FIG. 3B, the shutoff mechanism 244 is a float valve assembly in the form of a ball 244a which is held and suspended within a cage 244b positioned below a valve seat 244c disposed within the opening at the top of the container below the second port 243b that will float upon the exudate and will be lifted against the valve seat 244c as the container 243 fills with exudate. When the ball 244a is firmly seated against the valve seat 244c, the float valve blocks the second port 243b and thereby shuts off the source of suction from the vacuum system 250. In other embodiments of the container 243, other types of mechanisms may also be employed to detect the liquid level within the container 243 in order to arrest operation of the vacuum system 250. In addition, in various embodiments of this second aspect of the invention, the shutoff mechanism 244 may be comprised of any means that enables the vacuum system 250 to halt the supply of reduced pressure to the enclosure 220 at any time that the volume of exudate from the portion 215, 216 of the body to be treated exceeds a predetermined amount. Such means may include mechanical switches, electrical switches operably connected to the vacuum system controller 232, optical, thermal or weight sensors operably connected to the vacuum system controller 232, and any other means that are currently known in the relevant art or that may be developed in the art in the future.

In some embodiments of this second aspect of the invention, the treatment appliance 211 further comprises tissue protection means (not illustrated) to protect and strengthen the surface tissue of the portions 215, 216 of the body to be treated that are adjacent to the enclosure 220. The tissue protection means protects such tissue by preventing abrasion and maceration of the tissue. Preferably, the tissue protection means is a hydrocolloid material, such as COLOPLAST Hydrocolloid 2655, anhydrous lanoline, or any combination of such hydrocolloid materials. More preferably, the tissue protection means is COLOPLAST Hydrocolloid 2655. The tissue protection means may be applied to the body tissue to be protected, or it may be applied to the surface of the enclosure 220 that is to be in contact with the body tissue, or both, prior to placing the enclosure 220 over the surface of the portion 215, 216 of the body to be treated. It is to be noted that application of the tissue protection means to the body tissue that is adjacent to the enclosure 220 at the portion 215, 216 of the body to be treated may only entail application of the tissue protection means to the parts of the body tissue adjacent to the enclosure 220 that require such protection.

Referring to FIG. 3A, a method of using the treatment appliance 210 of the illustrated embodiment is also disclosed. In this example, the enclosure 220 is removed from an aseptic package in which it is stored. The enclosure 220 is then placed over and encloses the portion 215, 216 of the body to be treated, which is the wrist and hand portions 215, 216 in this example. The enclosure 220 is also connected to the vacuum system 250 by means of the port 128 on the enclosure 220 either before, after or during the placement of the enclosure 220 over the portion 215, 216 of the body to be treated. Where it is deemed necessary by the user of the treatment appliance 210, tissue protection means, as described above, may be placed on a portion of the enclosure 220, on the body tissue to be protected, or both, prior to placing the enclosure 220 over the portion 215, 216 of the body to be treated. In the example illustrated in FIG. 3A, the interior surface portions 229 of the enclosure 220 positioned around and adjacent to the perimeter 222 of the opening 221 of the enclosure 220 are in contact with (or can be deformed to be in contact with) the surrounding surface of the adjacent portion 214 of the body. Such deformation may be caused by the user of the treatment appliance 210 exerting mild pressure on the portions 225 of the enclosure 220 positioned around and adjacent to the perimeter 222 of the opening 221 of the enclosure 220 so that they are in contact with the surface of the adjacent portion 214 of the body. Reduced pressure is then supplied to the enclosure 220 by the vacuum system 150. When reduced pressure is applied to the volume under the enclosure 220 at the portion 215, 216 of the body to be treated, the enclosure 220 is drawn downward by the reduced pressure, collapsing the enclosure 220 in the approximate direction of the portion 215, 216 of the body to be treated. As the enclosure 220 collapses, the portions 225 of the enclosure 220 adjacent to the perimeter 222 of the opening 221 of the enclosure 220 are drawn tightly against the surface of the adjacent portion 214 of the body, thus forming an operable seal between the portions 225 of the enclosure 220 adjacent to the perimeter 222 of the opening 221 of the enclosure 220 and the portion 214 of the body adjacent to such portions 225. References to an "operable seal" and "sealing means" herein refer generally to a seal that may be made gas-tight and liquid-tight for purposes of the reduced pressure treatment of the portion 215, 216 of the body to be treated. It is to be noted that this seal need not be entirely gas-tight and liquid-tight. For example, the operable seal may allow for a relatively small degree of leakage, so that outside air may enter the volume under the enclosure 220 at the portion 215, 216 of the body to be treated, as long as the degree of leakage is small enough so that the vacuum system 250 can maintain the desired degree of reduced pressure in the volume under the enclosure 220 at the portion 215, 216 of the body to be treated. As another example, the operable seal formed by the enclosure 220 may not be solely capable of maintaining the reduced pressure in the volume under the enclosure 220 the portion 215, 216 of the body to be treated due to the shape of the body at the portion 215, 216 of the body to be treated or for other reasons. In these cases, as well as other cases, it may be necessary to provide other sealing means (not illustrated), which are used to provide a seal between the portions of the enclosure 220 and the portion 214 of the body where the operable seal is not adequate to permit reduced pressure to be maintained in the volume under the enclosure 220 at the portion 215, 216 of the body to be treated. For example, in the illustrated embodiment, the sealing means may be an adhesive applied to a portion of the enclosure 220 or a portion of the body in a manner similar to the application of the tissue protection means described above. In other embodiments, the sealing means may be comprised of almost any suitable means to provide an adequate seal. For example, the sealing means may be comprised of an adhesive, an adhesive tape, lanoline, a stretch fabric that covers the treatment device 211 and is wrapped around a portion 214 of the body of the patient at the portion 215, 216 of the body to be treated, or any combination of such means. It is also to be noted that in this embodiment at least one fold 227 forms in the surface of the enclosure 220 when it collapses, so that fluids aspirated by the portion 215, 216 of the body to be treated flow along the at least one fold 227 to the port 228, where the fluid is removed from the enclosure 220 by means of the reduced pressure supply means 240 cooperating with the reduced pressure supply source 230. Thus, in the preferred embodiments, the enclosure 220 is constructed of a material, and has a size, shape and thickness, that permits the enclosure 220 to collapse in the direction of the portion 215, 216 of the body to be treated and form an operable seal with a portion 214 of the body when reduced pressure is applied to the volume under the enclosure 220 at the portion 215, 216 of the body to be treated, while still being rigid enough to support the at least one fold 227. It is also to be noted that the volume under the enclosure 220 at the portion 215, 216 of the body to be treated may be minimal while the enclosure 220 is in its collapsed state over the portion 215, 216 of the body to be treated. In the preferred embodiments of this second aspect of the invention, the reduced pressure maintained in the volume under the enclosure 220 at the portion 215,216 of the body to be treated is in the range from approximately 20 mm of Hg below atmospheric pressure to approximately 125 mm of Hg below atmospheric pressure. In yet other embodiments, the reduced pressure is applied to the enclosure 220 in a cyclic nature, the cyclic nature providing alternating time periods of application of reduced pressure and non-application of reduced pressure. In all of these embodiments, the reduced pressure is maintained in the volume under the enclosure 220 at the portion 215, 216 of the body to be treated until such portion 215,216 has progressed toward a selected stage of healing.

An embodiment of a third aspect of the invention is the treatment appliance 310 illustrated in FIG. 4. In this embodiment, the treatment appliance 310 is comprised of a treatment device 311 and a vacuum system, generally designated 350, operably connected to, and providing a supply of reduced pressure to, the treatment device 311. In addition, in this embodiment, the vacuum system 350 is further comprised of a reduced pressure supply source, generally designated 360, which is described in more detail below, and reduced pressure supply means, generally designated 340, which are described in more detail below. Also in this embodiment, the treatment device 311 is further comprised of an enclosure 320, a liner 370, wound packing means 375, and a suction drain 345. In the embodiment of the third aspect of the invention illustrated in FIG. 4, the enclosure 320 has the structure, features, and characteristics illustrated in FIG. 4. It is to be noted, however, that in other embodiments of this third aspect of the invention, the enclosure 320 may have substantially the same structure, features, characteristics and operation as any embodiment of all of the enclosures 20, 120, 220, 320 of the first aspect of the invention described above and illustrated in connection with FIG. 1A, FIG. 1B, FIG. 1C, FIG. 2 and FIG. 3, respectively. In the embodiment illustrated in FIG. 4, the enclosure 320 is placed over and encloses the entire lower leg portion 317 of the patient and is used to treat a wound 318 on the patient's foot 319. The enclosure 320 is illustrated in a state of complete collapse, with the portion 325 of the enclosure 320 adjacent to the perimeter 322 of the opening 321 in the enclosure 320 forming an operable seal with the adjacent portions 314 of the lower leg portion 317. In these embodiments, the enclosure 320 may be sealed to the adjacent portions 314 of the body using any of the sealing means or operable seals described above and illustrated in connection with FIG. 3A.

In the embodiment of the third aspect of the invention illustrated in FIG. 4, the treatment device 311 is further comprised of wound packing means 375, which is placed in the area of the wound 318 under the enclosure 320. In this embodiment, a liner 370 is placed over the lower leg portion 317 (including the foot 319) of the patient, the wound 318, and the wound packing means 375. In this embodiment, the liner 370 may be used to hold the wound packing means 375 in place. In other embodiments, the liner 370 may also be used to provide additional comfort for the patient. The liner 370 may be comprised of any suitable material currently known in the art or developed in the art in the future that may be used for purposes of patient garments and similar purposes. For example, the liner 370 may be comprised of naturally occurring or synthetic fibers, fabrics or materials, such as cotton, polyester, nylon, and rayon, or any combination of all such fibers, fabrics and materials. Preferably, the liner 370 is constructed of a cotton-polyester blend. It is to be noted that the liner 370 may be used with other embodiments of the present invention, such as the embodiment described and illustrated in connection with FIG. 3A and FIG. 3B, above, with or without a suction drain 345 or wound packing means 375. In the illustrated embodiment, the enclosure 320 is placed over the lower leg portion 317 of the patient, including the liner 370, the wound 318, and the wound packing means 375 when the enclosure 320 is positioned on the surface of the body 317, 319 at the site of the wound 318. In some embodiments of this third aspect of the invention, the wound packing means 375 may be placed within the wound 318 to prevent overgrowth of the tissue in the area of the wound 318. For example, and preferably in these cases, the wound packing means 375 may be comprised of absorbent dressings, antiseptic dressings, nonadherent dressings, water dressings, or combinations of such dressings. More preferably, the wound packing means 375 may be comprised of gauze or cotton or any combination of gauze and cotton. In still other embodiments of this third aspect of the invention, the wound packing means 375 may be comprised of an absorbable matrix adapted to encourage growth of the tissue in the area of the wound 318 into the matrix. In these embodiments, the absorbable matrix (as wound packing means 375) is constructed of an absorbable material that is absorbed into the epithelial and subcutaneous tissue in the wound 318 as the wound 318 heals. The matrix (as wound packing means 375) may vary in thickness and rigidity, and it may be desirable to use a spongy absorbable material for the patients comfort if the patient must lie upon the treatment device 311 during treatment. The matrix (as wound packing means 375) may also be perforated and constructed in a sponge-type or foam-type structure to enhance gas flow and to reduce the weight of the matrix. Because of the absorbable nature of the absorbable matrix (as wound packing means 375), the matrix should require less frequent changing than other dressing types during the treatment process. In other circumstances, the matrix (as wound packing means 375) may not need to be changed at all during the treatment process. In some embodiments of this third aspect of the invention, the absorbable matrix (as wound packing means 375) may be comprised of collagens or other absorbable materials or combinations of all such materials. U.S. patent application Ser. No. 10/652,100, which was filed by one of the present inventors with the U.S. Patent and Trademark Office on Aug. 28, 2003, and is hereby incorporated by reference, also discloses various embodiments of an absorbable matrix that may be utilized with various embodiments of this third aspect of the present invention. It is to be noted, however, that wound packing means 375 may not be utilized in other embodiments of this third aspect of the invention.

In the embodiment of the third aspect of the invention illustrated in FIG. 4, the treatment device 311 is also comprised of a suction drain 345 and suction drain connection means, which are described in more detail below, to operably connect the reduced pressure supply means 340 to the suction drain 345 so that the suction drain 345 is in fluid communication with the reduced pressure supply means 340 and reduced pressure is supplied to the volume under the enclosure 320 in the area of the wound 318 by means of the suction drain 345. In this embodiment, the suction drain 345 is further comprised of a bottom drain portion 345a extending into the area of the wound 318 under the enclosure 320 from a top drain portion 345b positioned within the volume of the enclosure and extending to connect to the reduced pressure supply means 340. In the illustrated embodiment, the top drain portion 345b is positioned adjacent to the interior surface of the enclosure 320 and is directly connected to the reduced pressure supply means 340 by means of a connector 346. In other embodiments, the top drain portion 345b may be attached to a port located in the enclosure 320, which may be positioned on the enclosure 320 in the same manner that the port 228 is located on the enclosure 220, as described and illustrated above in connection with FIG. 3A. In these embodiments, the top drain portion 345b is attached to the opening on the side of the port that is opposite the side of the port opening that is connected to the reduced pressure supply means 340. In some of these embodiments, the top drain portion 345b may be permanently or removably attached to the interior surface of the opening of the port using any suitable means, such as an adhesive, or by the top drain portion 345b having a shape adapted so that all or a portion of it fits tightly against all or a portion of the interior surface of the opening in the port. The suction drain system disclosed in U.S. patent application Ser. No. 11/026,733, entitled "Improved Reduced Pressure Wound Treatment Appliance," which was filed by one of the present inventors with the U.S. Patent and Trademark Office on Dec. 30, 2004, may also be used in conjunction with the present invention. The disclosure of this U.S. patent application is incorporated herein by reference. In the illustrated embodiment, it is to be noted that the top drain portion 345b must be sufficiently sealed against the surface of the enclosure 320 and the portion 314 of the body adjacent to the opening 321 in a manner so that reduced pressure can be maintained in the volume under the enclosure 320 in the area of the wound 318. In the embodiment illustrated in FIG. 3, the top drain portion 345b and the bottom drain portion 345a of the suction drain 345 are comprised of polymer tubing that is flexible enough to allow the tubing to easily bend, but rigid enough to prevent the tubing from collapsing during use. In other embodiments, portions of the top drain portion 345b and the bottom drain portion 345a of the suction drain 345 may be comprised of other materials, such as flexible or semi-rigid polymers, plastics, rubber, silicone, or combinations of such materials. In yet other embodiments, the suction drain 345 may have different cross-sectional shapes, such as elliptical, square, rectangular, pentagonal, hexagonal, or other shapes. In still other embodiments, the bottom drain portion 345a of the suction drain 345 may be further comprised of wound suction means that may be used to remove debris, exudate and other matter from the wound 318. In the embodiment illustrated in FIG. 3, the wound suction means is comprised of a distal end portion 345a' of the tubing comprising the bottom drain portion 345a having a plurality of perforations 245a" in the surface of the distal end portion 345a'. In other embodiments, the distal end portion 345a' of the bottom drain portion 345a may have almost any shape or combination of shapes (e.g., circular, elliptical, square, pentagonal, or hexagonal), including a shape different from the remaining portion of the bottom drain portion 345a, may be of almost any size relative to the remaining bottom drain portion 345a (e.g., may be longer or shorter than the remaining bottom drain portion 345a or have a cross-section smaller or larger than the remaining bottom drain portion 345a, or both), may have more or fewer perforations 345a", may have different sizes and shapes of perforations 345a", may extend along different portions of the bottom drain portion 345a, and may be constructed in whole or in part of materials that are not flexible. In embodiments that have a distal end portion 345a', the distal end portion 345a' may be attached to the remaining portion of the bottom drain portion 345a in almost any manner, as long as the remaining bottom drain portion 345a is in fluid communication with the wound suction means 345a'. Examples include an adhesive in some embodiments and a fastening collar in other embodiments. In still other embodiments, the distal end portion 345a' may be fused or welded to the remaining portion of the bottom drain portion 345a. In yet other embodiments, the distal end portion 345a' and the remaining portion of the bottom drain portion 345a may be fabricated as a single piece.

In some embodiments of this third aspect of the invention, as illustrated in FIG. 4, the top drain portion 345b may extend beyond the opening 321 of the enclosure 320 into the area outside the volume of the enclosure 320. In some of these embodiments, as is also illustrated in FIG. 4, the suction drain connection means, which may be used to removably connect the reduced pressure supply means 340 to the top drain portion 345b of the suction drain 345 is a variable descending diameter adapter 346 (commonly referred to as a "Christmas tree" adapter) that is placed into the interior volume of the top drain portion 345b at its distal end. In other embodiments, the suction drain connection means may be clamps, fastening collars, luer lock fittings and adapters, or other fasteners or combinations thereof. In yet other embodiments, the top drain portion 345b may be fused or welded to the reduced pressure supply means 340. In still other embodiments, the top drain portion 345b and the portion of the reduced pressure supply means 340 adjacent to the top drain portion 345b may be fabricated as a single piece.

In the embodiment of this third aspect of the invention illustrated in FIG. 4, the distal end portion 345a' of the suction drain 345 extends into the interior volume of the wound packing means 375. In this embodiment, the wound packing means 375 and the suction drain 345 may be fabricated by snaking the distal end portion 345a' of the suction drain 345 through an internal passageway in the wound packing means 375, such as by pulling the distal end portion 345a' of the suction drain 345 through the passageway using forceps. Alternatively, the wound packing means 375 and the suction drain 345 may be manufactured as a single piece in sterile conditions and then be stored in an aseptic package until ready for use. In other embodiments, the distal end portion 345a' of the suction drain 345 may be placed adjacent or close to the wound packing means 375 in the area of the wound 318. The preferred means of placement of the suction drain 345 relative to the wound packing means 375 is dependent upon the type of wound 318, the type of wound packing means 375, and the type of treatment desired. Referring to FIG. 4 as an example, it is therefore to be noted that in some embodiments of this third aspect of the invention, the wound treatment device 311 may utilize a suction drain 345 without utilizing wound packing means 375, while in other embodiments a suction drain 345 may be utilized with wound packing means 375. In addition, in other embodiments of this third aspect of the invention, the wound treatment device 311 may utilize wound packing means 375 without utilizing a suction drain 345, while in other embodiments wound packing means 375 may be utilized with a suction drain 345.

In the embodiment of the third aspect of the invention illustrated in FIG. 4, the vacuum system 350 is generally comprised of a suction bulb 361 having an inlet port 362 and an outlet port 363, a bulb connection tubing member 364, an exhaust tubing member 365, an exhaust control valve 366, a filter 367, and a supplemental vacuum system (illustrated schematically and generally designated 350a). In this embodiment, the suction bulb 361 is a hollow sphere that may be used to produce a supply of reduced pressure for use with the treatment device 311. In addition, the suction bulb 361 may also be used to receive and store fluid aspirated from the wound 318. The inlet port 362 of the suction bulb 361 is connected to one end of the bulb connection tubing member 364, which is also the reduced pressure supply means 340 in this embodiment. The connection tubing member 364 is connected by suction drain connection means to the top drain portion 345b at its other end in a manner so that the interior volume of the suction bulb 361 is in fluid communication with the suction drain 345. In this embodiment, the bulb connection tubing member 364 is sufficiently flexible to permit movement of the bulb connection tubing member 364, but is sufficiently rigid to resist constriction when reduced pressure is supplied to the suction drain 345 or when the location of the wound 318 is such that the patient must sit or lie upon the bulb connection tubing member 364 or upon the treatment device 311. The outlet port 363 of the suction bulb 361 is connected to the exhaust tubing member 365. In this embodiment, the exhaust tubing member 365 is sufficiently flexible to permit movement of the exhaust tubing member 365, but is sufficiently rigid to resist constriction when reduced pressure is supplied to the suction drain 345. The inlet port 362 of the suction bulb 361 may be connected to the bulb connection tubing member 364 and the outlet port 363 of the suction bulb 361 may be connected to the exhaust tubing member 365 using any suitable means, such as by welding, fusing, adhesives, clamps, or any combination of such means. In addition, in some embodiments, which are the preferred embodiments, the suction bulb 361, the bulb connection tubing member 364, and the exhaust tubing member 365 may be fabricated as a single piece. In the illustrated embodiment, the exhaust control valve 366 and the filter 367 are operably connected to the exhaust tubing member 365. In this embodiment, the exhaust control valve 366 is used to regulate the flow of fluids (gases and liquids) to and from the suction bulb 361 and the supplemental vacuum system 350a. In embodiments of the invention that do not have a supplemental vacuum system 350a, the exhaust control valve 366 regulates flow of fluids to and from the suction bulb 361 and the outside atmosphere. Generally, the exhaust control valve 366 allows fluids to flow out of the suction bulb 361 through the outlet port 363, but not to flow in the reverse direction unless permitted by the user of the appliance 310. Any type of flow control valve may be used as the exhaust control valve 366, as long as the valve 366 is capable of operating in the anticipated environment involving reduced pressure and wound 318 exudate. Such valves are well known in the relevant art, such as sprung and unsprung flapper-type valves and disc-type valves, operating in conjunction with or without ball, gate and other similar types of valves. In this embodiment, the filter 367 is operably attached to the exhaust tubing member 365 between the outlet port 363 of the suction bulb 361 and the exhaust control valve 366. The filter 367 prevents potentially pathogenic microbes or aerosols from contaminating the exhaust control valve 366 (and supplemental vacuum system 350a), and then being vented to atmosphere. The filter 367 may be any suitable type of filter, such as a micropore filter. In other embodiments, the filter 367 may also be a hydrophobic filter that prevents any exudate from the wound 318 from contaminating the exhaust control valve 366 (and the supplemental vacuum system 350a) and then being vented to atmosphere. In still other embodiments, the filter 367 may perform both functions. It is to be noted, however, that the outlet port 363, the exhaust control valve 366, the filter 367, or any combination of the exhaust control valve 366 and the filter 367, need not be utilized in connection with the vacuum system 350 in other embodiments of the invention.

In some embodiments of the third aspect of the invention illustrated in FIG. 4 that do not utilize a supplemental vacuum system 350a, the suction bulb 361 may be used to produce a supply of reduced pressure in the following manner. First, the user of the appliance 310 appropriately seals all of the component parts of the appliance 310 in the manner described herein. For example, the enclosure 320 is placed over and encloses the portion 317, 319 of the body to be treated, as well as any other components within the volume of the enclosure 320, such as the liner 370, wound packing means 375, and the suction drain 345. At least the portion 325 of the enclosure 320 adjacent to the opening 321 of the enclosure 320 is sealed (or placed adjacent) to the adjacent portions 314 of the body and the suction drain 345, and the suction drain 345 is connected to the bulb connection tubing member 364 by means of the connector 346. The user then opens the exhaust control valve 366 and applies force to the outside surface of the suction bulb 361, deforming it in a manner that causes its interior volume to be reduced. When the suction bulb 361 is deformed, the gas in the interior volume is expelled to atmosphere through the outlet port 363, the exhaust tubing member 365, the filter 367, and the exhaust control valve 366. The user then closes the exhaust control valve 366 and releases the force on the suction bulb 361. The suction bulb 361 then expands, drawing fluid (liquid and gas) from the area of the wound 318 under the treatment device 311 into the suction bulb 361 through the suction drain 345 and causing the pressure in such area to decrease. To release the reduced pressure, the user of the appliance 310 may open the exhaust control valve 366, allowing atmospheric air into the interior volume of the suction bulb 361. The level of reduced pressure may also be regulated by momentarily opening the exhaust control valve 366.

The suction bulb 361 may be constructed of almost any fluid impermeable flexible or semi-rigid material that is suitable for medical use and that can be readily deformed by application of pressure to the outside surface of the suction bulb 361 by users of the appliance 310 and still return to its original shape upon release of the pressure. For example, the suction bulb 361 may be constructed of rubber, neoprene, silicone, or other flexible or semi-rigid polymers, or any combination of all such materials. In addition, the suction bulb 361 may be of almost any shape, such as cubical, ellipsoidal, or polygonal. The suction bulb 361 may also be of varying size depending upon the anticipated use of the suction bulb 361, the size of the wound treatment device 311, use of a supplemental vacuum system 350a, the level of reduced pressure desired, and the preference of the user of the appliance 310. In the embodiment of the invention illustrated in FIG. 4, the supplemental vacuum system 350a is connected to the exhaust tubing member 365 and is used to provide a supplemental supply of reduced pressure to the suction bulb 361 and treatment device 311. In this embodiment, the supplemental vacuum system 350a may have substantially the same structure, features, characteristics and operation of the various embodiments of the vacuum system 250 of the first version of the invention described above and illustrated in connection with FIG. 3A and FIG. 3B. It is to be noted, however, that the supplemental vacuum system 350a need not be used in connection with the vacuum system 350 in other embodiments of the invention.

Except as described below, the treatment appliance 310 described above and illustrated in connection with FIG. 4 may generally be used in a manner similar to the treatment appliance 210 described above and illustrated in connection with FIG. 3A and FIG. 3B. As a result, except as described below, the example of how the embodiment of the treatment appliance 210 and the enclosure 220 described above and illustrated in connection FIG. 3A may be used in treatment of a portion 215, 216 of a body also applies to the embodiment of the appliance 310 of the third aspect of the invention described above and illustrated in connection with FIG. 4. In the case of the embodiment illustrated in FIG. 4, however, the wound packing means 375 is placed into the wound 318, the suction drain 345 is installed, and the liner 370 is placed over the portion 317, 319 of the body to be treated prior to placement of the enclosure 320 over the portion 317, 319 of the body to be treated. In addition, the enclosure 320 is placed over the wound packing means 375, a portion of the suction drain 345, and the liner 370. In embodiments where the distal end portion 345a' of a suction drain 345 is placed into the interior volume of, or adjacent to, the wound packing means 375, the distal end portion 345a' of the suction drain 345 is also placed in the appropriate position before the enclosure 320 is placed over the portion 317, 319 of the body to be treated. In embodiments utilizing a suction drain 345 without wound packing means 375, the suction drain 345 is installed in the enclosure 320 before the enclosure 320 is placed over the portion 317, 319 of the body to be treated. In embodiments utilizing a liner 370 without wound packing means 375 or suction drain 345, the liner 370 is positioned over the portion 317, 319 of the body to be treated before the enclosure 320 is placed over such portion 317, 319 of the body

What is claimed is:
1. A method of treating an extremital portion of a human body, such method comprising the steps of:
positioning a flexible enclosure having an opening over the extremital portion of the body to be treated, wherein the enclosure is sized to be placed over and completely enclose the extremital portion of the body to be treated and adapted to maintain reduced pressure at the extremital portion of the body to be treated, and wherein the extremital portion of the body to be treated is selected from the group consisting of an arm, a leg, and any extremital regions thereof;

sealing the area of the enclosure adjacent to the opening to the body, so that reduced pressure may be maintained in the volume under the enclosure at the portion of the body to be treated;

operably connecting the enclosure with a vacuum system for producing reduced pressure in the volume under the enclosure at the portion of the body to be treated, such that application of reduced pressure causes substantially all of the enclosure to deform to substantially conform to a majority of the contours of the extremital portion of the body to be treated;

removing fluid from the volume under the enclosure at the portion of the body to be treated via the application of reduced pressure;

storing fluid removed from the volume under the enclosure in a collection system; and maintaining the reduced pressure under the enclosure at the portion of the body being treated.

2. The method of claim 1, wherein the vacuum system is comprised of a suction bulb and the step of operably connecting the enclosure with the vacuum system further comprises the step of squeezing the suction bulb to reduce its volume and then releasing the suction bulb, so that reduced pressure is produced in the volume under the enclosure at the portion of the body to be treated.

3. The method of claim 1, wherein the reduced pressure under the enclosure at the portion of the body to be treated is in the range from approximately 20 mm of Hg below atmospheric pressure to approximately 125 mm of Hg below atmospheric pressure.

4. The method of claim 1, wherein the reduced pressure is applied cyclically.

5. The method of claim 1, further comprising the step of placing a wound packing mechanism between the portion of the body to be treated and the enclosure, such step being performed prior to positioning the enclosure over the portion of the body to be treated.

6. The method of claim 1, further comprising the step of placing a liner over the portion of the body to be treated, wherein the liner is disposed between the portion of the body to be treated and the enclosure, such step being performed prior to positioning the enclosure over the portion of the body to be treated.

7. The method of claim 1, wherein positioning the enclosure over the portion of the body to be treated occurs before coupling the enclosure with a vacuum system for producing reduced pressure in the volume under the enclosure at the portion of the body to be treated.

8. The method of claim 1, wherein positioning the enclosure over the portion of the body to be treated occurs after operably connecting the enclosure with a vacuum system for producing reduced pressure in the volume under the enclosure at the portion of the body to be treated.

9. The method of claim 1, wherein the collection system comprises a canister.

10. The method of claim 9, wherein the canister is positioned between the flexible enclosure and the vacuum system, the canister disposed outside the flexible enclosure.

11. The method of claim 1, wherein the fluid is a liquid.

12. A method of treating an extremital portion of a human body, such method comprising the steps of:

positioning a flexible enclosure having an opening over the portion of the body to be treated, wherein the enclosure is sized to be placed over and completely enclose the portion of the body to be treated, wherein the enclosure is adapted to maintain reduced pressure at the portion of the body to be treated and configured to substantially completely deform to substantially conform to a majority of the contours of the portion of the body to be treated, and wherein the portion of the body to be treated is selected from the group consisting of an arm, a leg, and any extremital regions thereof;

operably connecting the enclosure with a vacuum system for producing reduced pressure in the volume under the enclosure;

sealing the area of the enclosure adjacent the opening to the body, so that reduced pressure may be maintained in the volume under the enclosure at the portion of the body to be treated;

applying reduced pressure to the volume under the enclosure at the portion of the body to be treated such that fluid may be removed therefrom; and storing fluid removed from the volume under the enclosure in a collection system.

13. The method of claim 12, wherein positioning the enclosure having an opening over the portion of the body to be treated occurs after operably connecting the enclosure with a vacuum system for producing reduced pressure in the volume under the enclosure at the portion of the body to be treated.

14. The method of claim 12, wherein positioning the enclosure having an opening over the portion of the body to be treated occurs before coupling the enclosure with a vacuum system for producing reduced pressure in the volume under the enclosure at the portion of the body to be treated.

15. The method of claim 12, wherein the collection system comprises a canister.

16. The method of claim 15, wherein the canister is positioned between the flexible enclosure and the vacuum system, the canister disposed outside the flexible enclosure.

17. The method of claim 12, wherein the fluid is a liquid.

18. A method of treating an extremital portion of a human body, such method comprising the steps of:

operably connecting an enclosure having an opening with a vacuum system, wherein the enclosure is sized to be placed over and completely enclose the portion of the body to be treated, the enclosure is configured to substantially completely deform to substantially conform to a majority of the contours of the portion of the body to be treated and adapted to maintain reduced pressure at the portion of the body to be treated, and the vacuum system produces reduced pressure for the volume under the enclosure at the portion of the body to be treated;

positioning the enclosure over the portion of the body to be treated, wherein the portion of the body to be treated is selected from the group consisting of an arm, a leg, and any extremital regions thereof;

sealing the area of the enclosure adjacent to the opening to the body, so that reduced pressure may be maintained in the volume under the enclosure at the portion of the body to be treated;

removing fluid from the volume under the enclosure at the portion of the body to be treated with the vacuum system;

storing fluid removed from the volume under the enclosure in a collection system; and applying the reduced pressure under the enclosure at the portion of the body being treated.

19. The method of claim 18, wherein operably connecting the enclosure having an opening with a vacuum system occurs before positioning the enclosure over the portion of the body to be treated.

20. The method of claim 18, wherein coupling the enclosure having an opening with a vacuum system occurs after positioning the enclosure over the portion of the body to be treated.

21. The method of claim 18, wherein the collection system comprises a canister.

22. The method of claim 21, wherein the canister is positioned between the enclosure and the vacuum system, the canister disposed outside the enclosure.

23. The method of claim 18, wherein the fluid is a liquid.

\* \* \* \* \*

UNITED STATES PATENT AND TRADEMARK OFFICE
CERTIFICATE OF CORRECTION

| | | |
|---|---|---|
| PATENT NO. | : 8,708,998 B2 | Page 1 of 2 |
| APPLICATION NO. | : 12/419542 | |
| DATED | : April 29, 2014 | |
| INVENTOR(S) | : Weston et al. | |

It is certified that error appears in the above-identified patent and that said Letters Patent is hereby corrected as shown below:

On the Title Page, References Cited

Column 2 (page 3, item 56) line 18, Under Other Publications, change "Insturments," to --Instruments,--.

Column 2 (page 3, item 56) line 26, Under Other Publications, change "Intraperiotoneal" to --Intraperitoneal--.

Column 1 (page 4, item 56) line 28, Under Other Publications, change "Fistual" to --Fistula--.

Column 1 (page 4, item 56) line 40, Under Other Publications, change "intemet" to --internet--.

Column 2 (page 4, item 56) line 2, Under Other Publications, change "Bulbocavernous" to --Bulbocavernosus--.

Column 2 (page 4, item 56) line 64, Under Other Publications, change "Statis" to --Stasis--.

Column 2 (page 4, item 56) line 65, Under Other Publications, change "Diastolid" to --Diastolic--.

Column 1 (page 5, item 56) line 13, Under Other Publications, change "Controled" to --Controlled--.

Column 1 (page 5, item 56) line 60, Under Other Publications, change "intemet" to --internet--.

Column 2 (page 5, item 56) line 1, Under Other Publications, change "Variag," to --Verlag,--.

Column 2 (page 5, item 56) line 15, Under Other Publications, change "Iliostomy" to --Ileostomy--.

Column 2 (page 6, item 56) line 27, Under Other Publications, change "Voluje" to --Volume--.

Signed and Sealed this
Seventh Day of October, 2014

Michelle K. Lee
*Deputy Director of the United States Patent and Trademark Office*

CERTIFICATE OF CORRECTION (continued)
U.S. Pat. No. 8,708,998 B2

Column 1 (page 7, item 56) line 25, Under Other Publications, change "Pressue" to --Pressure--.

Column 2 (page 7, item 56) line 25, Under Other Publications, change "Gynnecology" to --Gynecology--.

Column 1 (page 9, item 56) line 7, Under Other Publications, change "Pecularities" to --Peculiarities--.

In the Specification

Column 7 at line 37, Change "patients" to --patient's--.

Column 9 at line 33, Change "patients" to --patient's--.

Column 20 at line 2, Change "patients" to --patient's--.

Column 24 at line 60, Change "body" to --body.--.